US009778282B2

(12) United States Patent
Yang et al.

(10) Patent No.: US 9,778,282 B2
(45) Date of Patent: Oct. 3, 2017

(54) METHOD AND APPARATUS FOR INFRARED SCATTERING SCANNING NEAR-FIELD OPTICAL MICROSCOPY WITH HIGH SPEED POINT SPECTROSCOPY

(71) Applicant: Anasys Instruments, Santa Barbara, CA (US)

(72) Inventors: Honghua Yang, Santa Barbara, CA (US); Kevin Kjoller, Santa Barbara, CA (US); Sam Berweger, Boulder, CO (US); Craig Prater, Santa Barbara, CA (US)

(73) Assignee: Anasys Instruments, Santa Barbara, CA (US)

( * ) Notice: Subject to any disclaimer, the term of this patent is extended or adjusted under 35 U.S.C. 154(b) by 0 days.

(21) Appl. No.: 15/488,240

(22) Filed: Apr. 14, 2017

(65) Prior Publication Data

US 2017/0219622 A1    Aug. 3, 2017

Related U.S. Application Data

(63) Continuation-in-part of application No. 14/322,768, filed on Jul. 2, 2014, now Pat. No. 9,372,154, which is a continuation-in-part of application No. 13/835,312, filed on Mar. 15, 2013, now Pat. No. 8,793,811.

(51) Int. Cl.
| | |
|---|---|
| *G01Q 60/18* | (2010.01) |
| *G01N 21/47* | (2006.01) |
| *G01N 21/35* | (2014.01) |

(52) U.S. Cl.
CPC ............. *G01Q 60/18* (2013.01); *G01N 21/35* (2013.01); *G01N 21/47* (2013.01); *G01N 2201/0612* (2013.01); *G01N 2201/10* (2013.01)

(58) Field of Classification Search
USPC ................................ 850/6, 9, 30, 33; 73/105
See application file for complete search history.

(56) References Cited

U.S. PATENT DOCUMENTS

| | | | | |
|---|---|---|---|---|
| 9,658,247 B2 * | 5/2017 | Yang | ...................... | G01Q 20/02 |
| 2008/0285041 A1 * | 11/2008 | Ocelic | .................... | B82Y 20/00 |
| | | | | 356/450 |

* cited by examiner

*Primary Examiner* — Kiet T Nguyen
(74) *Attorney, Agent, or Firm* — Mark Rodgers

(57) ABSTRACT

This invention involves measurement of optical properties of materials with sub-micron spatial resolution through infrared scattering scanning near field optical microscopy (s-SNOM). Specifically, the current invention provides substantial improvements over the prior art by achieving high signal to noise, high measurement speed and high accuracy of optical amplitude and phase. Additionally, it some embodiments, it eliminates the need for an in situ reference to calculate wavelength dependent spectra of optical phase, or absorption spectra. These goals are achieved via improved asymmetric interferometry where the near-field scattered light is interfered with a reference beam in an interferometer. The invention achieves dramatic improvements in background rejection by arranging a reference beam that is much more intense than the background scattered radiation. Combined with frequency selective demodulation techniques, the near-field scattered light can be efficiently and accurately discriminated from background scattered light. These goals are achieved via a range of improvements including a large dynamic range detector, careful control of relative beam intensities, and high bandwidth demodulation techniques. In other embodiments, phase and amplitude stability are improved with a novel s-SNOM configuration. In other embodiments an absorption spectrum may be obtained directly by comparing properties from a known and unknown region of a sample as a function of illumination center wavelength.

26 Claims, 19 Drawing Sheets

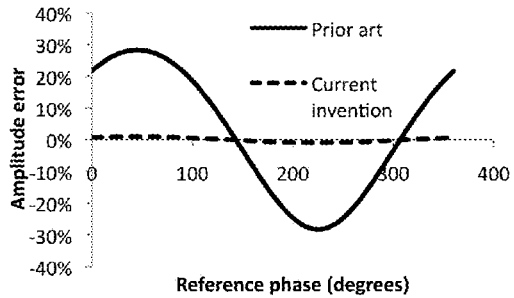
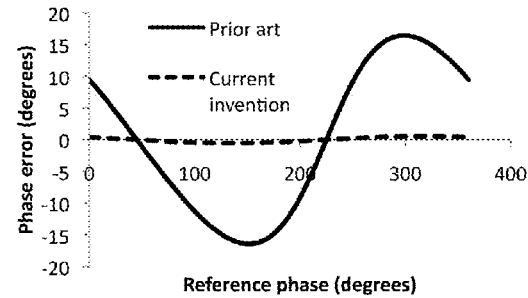
Fig. 4A  Fig. 4B
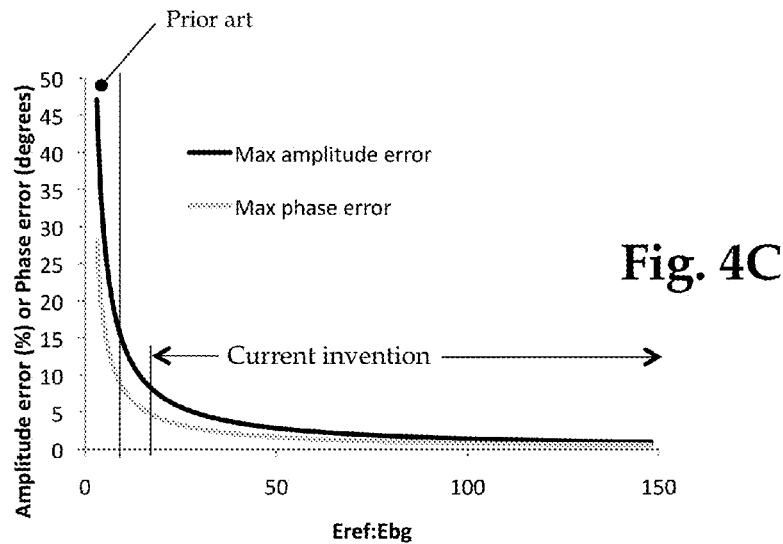
Fig. 4C
| $E_{ref}:E_{bg}$ ratio | Amplitude error (%) | Amplitude accuracy improvement | Phase error (deg) | Phase accuracy improvement |
|---|---|---|---|---|
| 5.00 | 28.28 | Prior art = 1 | 16.43 | Prior art = 1 |
| 20.00 | 7.07 | 4.00 | 4.08 | 4.03 |
| 50.00 | 2.83 | 10.00 | 1.63 | 10.14 |
| 150.00 | 0.94 | 29.99 | 0.54 | 30.42 |
Fig. 4D

Fig. 9A Raw spectrum
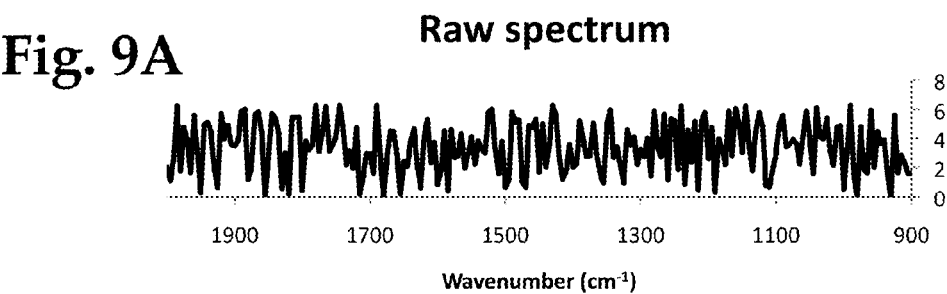
Fig. 9B Corrected by phase table
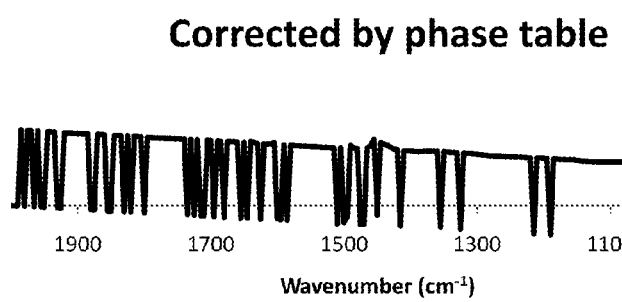
Fig. 9C Unwrapped
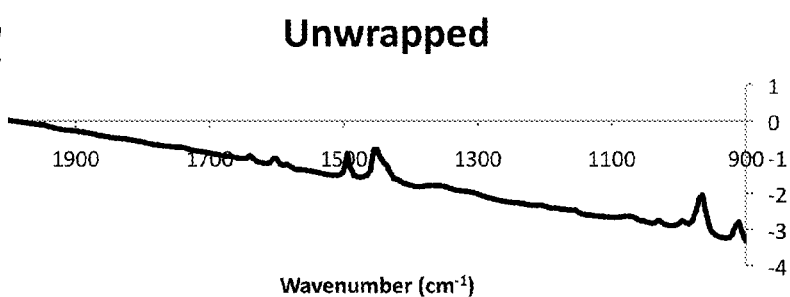
Fig. 9D Linear baseline corrected
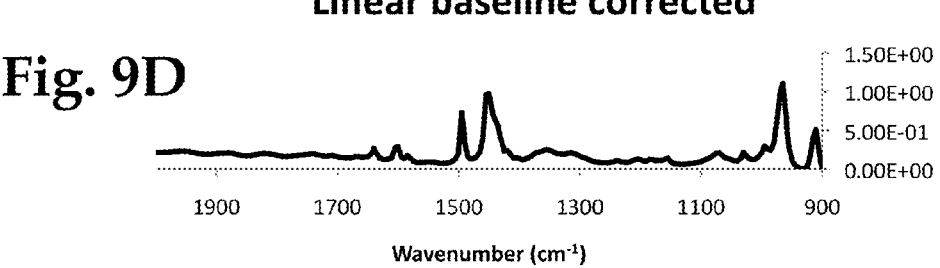

METHOD AND APPARATUS FOR INFRARED SCATTERING SCANNING NEAR-FIELD OPTICAL MICROSCOPY WITH HIGH SPEED POINT SPECTROSCOPY

RELATED APPLICATIONS

This application is a Continuation of U.S. application Ser. No. 14/634,859, filed Mar. 1, 2015 which is a Continuation-in-Part of U.S. application Ser. No. 14/322,768, filed Jul. 2, 2014 which is in turn a Continuation-in-Part of U.S. application Ser. No. 13/835,312, filed Mar. 15, 2013

BACKGROUND OF THE INVENTION

Scattering scanning near field optical microscopy (s-SNOM) operates by interacting a sharp probe tip of a probe microscope with a sample surface and collecting light scattered from the region of tip-sample interaction. Using this technique it is possible to measure the optical properties of samples with a spatial resolution far below the conventional diffraction limits. The resolution improvement comes from a local enhancement of the incident radiation field due to the sharp tip. The enhanced radiation field interacts with the sample and then scatters radiation into the far field. This near-field enhancement increases the amount of radiation scattered from the tip-sample region such that the scattered radiation can be more easily detected.

Referring to FIG. 1B, a probe 100 with a sharp tip 104 is interacted with a region of interest 106 of a sample 108. Light 110 with electric field intensity Ein is incident on the surface of a sample 108. The incident radiation field is enhanced in the region of the tip apex 104, leading to light scattered from the region of tip-sample interaction with electric field intensity Enf. It is the goal of a s-SNOM system to detect this scattered near field radiation Enf. Unfortunately, the incident radiation Ein also interacts with regions of the probe tip 102 that are away from the tip apex 104 and also with regions of the sample 108 that are away from the tip apex and even away from the region of interest 106. These unwanted interactions result in large background scattering Ebg. In practice, the background scattered field can be orders of magnitude larger than the tip apex scattered field Enf. For this reason it is highly desirable to have effective techniques to discriminate between light scattered from the tip apex region versus scattered from other sources.

Several techniques have been used to attempt to separate the near field light (scattered from the tip apex area) from background scattered light. A commonly used approach is to oscillate the tip, for example using the tip of an atomic force microscope and oscillating it at resonance, such as in tapping mode. Since the amount of near field light scattered from the sample depends strongly on the tip-sample distance, oscillating the tip in and out of contact with the surface modulates the light scattered into the far field. Several approaches have been used to demodulate the tip-scattered light from an oscillating AFM tip. The simplest approach is to use a lock-in amplifier to measure an amplitude of tip-scattered light at the oscillation frequency or a higher harmonic of this oscillation frequency. Stephen Quake also demonstrated the technique of time gating collection of tip scattered photons from fluorescence to correspond with the times that the tip is closest to the sample as described in U.S. Pat. No. 6,953,927.

While each of these approaches has achieved experimental success, each has significant limitations. In the case of simple oscillation of the tip with lock-in detection, the amount of light scattered into the far field depends on both the real and imaginary coefficients of the sample index of refraction and on an unknown arbitrary phase, as well as an unknown and variable amount of background scattering.

Interferometric techniques have also been used to improve detection of tip scattered light. There have been two main approaches, so called "homodyne" approach as described by Taubner et al in Journal of Microscopy, Vol. 210, Pt 3 Jun. 2003, pp. 311-314 and a "pseudoheterodyne" approach as described by Ocelic, Hillenbrand and others, for example in U.S. Pat. No. 7,738,115.

These interferometric techniques are shown generically and schematically in FIG. 1A. Light 122 from a light source 120 is directed through a beam splitter 124 to a sample 126 near the end 128 of probe 130. As indicated in prior description of FIG. 1B, the light incident on the probe and sample, results in light scattered both from the region of interest (Enf) and from background sources (Ebg). This scattered light can be directed back to the beam splitter 124 and then focused on a detector 140. The prior art has also employed well known interferometric techniques by directing a portion 134 of the incident beam at the beam splitter 124 to a reference mirror 136 and then interfering the reference beam with the sample scattered light at the detector 140. A modulator 138 may be used to periodically modulate the reference phase. This interferometric scheme is employed for three main purposes: (1) To provide wavelength sensitive measurements with broadband sources, as commonly performed with Fourier Transform Infrared (FTIR) spectroscopy; (2) to provide amplification for the weak tip-scattered field Enf, as will be explained below; (3) to provide separate measurements of the optical amplitude and phase.

We next consider the signal measured at the detector 140. The total electric field Etot at the detector is given by:

$$E_{tot} = E_{nf} + E_{bg} + E_{ref}$$

where each of these quantities are complex, to account for phase differences between the electric field components. Note that for simplicity, all collection efficiency factors and optical losses are being subsumed into the electric field strengths, i.e., these are the electric field strengths at the detector surface, not at the sources. The light intensity at the detector is proportional to |Etot|2, thus:

$$I_d \propto (E_{nf}^2 + E_{bg}^2 + E_{ref}^2 + 2E_{nf}E_{bg} + 2E_{nf}E_{ref} + 2E_{bg}E_{ref})$$

The interferometric scheme in FIG. 1A provides amplification of the near field scattered radiation through the crossterm ErefEnf. Unfortunately, in practice, there have been severe practical limits on amount of this amplification. Worse still, the background scattered light and reference beam light often have similar order of magnitude, and at best have a ratio of Eref:Ebg of ~3-10 (see for example U.S. Pat. No. 7,738,115, col. 2, lines 64ff). The fact that the reference intensity and background intensity are similar can lead to large errors in measurements of optical phase.

U.S. Pat. No. 7,738,115 describes method of overcoming these errors by separating near field and background fields using a "pseudoheterodyne" technique that uses sinusoidal oscillations of both the probe (130 in FIG. 1) and the reference mirror (138) to isolate the near field term Enf in frequency space. Using narrow band lock-in detection, this technique can obtain optical amplitude and phase measurements for the near field scattered radiation.

There are several disadvantages of the pseudoheterodyne approach, namely (1) loss in signal-to-noise; (2) loss in measurement speed; and (3) increased measurement complexity. The loss in signal-to-noise ratio comes from the fact that the pseudoheterodyne technique distributes the energy from the Enf signal across many frequency bands, specifically numerous sidebands around the cantilever oscillation frequency and its higher harmonics. (See for example FIG. 7 in U.S. Pat. No. 7,738,115 and the illustration in FIG. 3A). Thus demodulating at any single side band samples only a small portion of the original scattered energy. As a result the signal to noise ratio of the measurement is degraded—in the effort to reject background, much of the signal is discarded.

Additionally, the sidebands are very close to the original probe modulation frequency (and its harmonics). Specifically, the sidebands are separated from the cantilever oscillation frequencies by fref, the modulation frequency of the reference arm mirror. The reference arm mirror and associated actuators are relatively large mechanical devices and thus limited in practice to oscillations in the 100's of Hertz range. As such, it is necessary to demodulate the sidebands with a very narrow bandwidth lock-in amplifier, compared to the oscillation frequency of the probe which can be in the megahertz range. The narrow bandwidth required to demodulate the sideband thus slows down the measurement since it requires longer integration times and thus makes the entire measurement much slower.

The current invention overcomes these limitations by providing an optical arrangement that enables Eref>>Ebg. This allows direct demodulation of the scattered near field optical signal with high accuracy measurements of both optical amplitude and phase. Additionally, the technique of the current invention achieves much better signal-to-noise ratio as it can capture a much larger fraction of the signal in fewer and widely spaced frequency bands. This both substantially simplifies and speeds up the demodulation, thus supporting higher speed imaging and spectroscopy.

Another major limitation of prior art s-SNOM systems is the inability to easily calculate a spectrum that closely resembles a traditional infrared absorption spectrum without complicated post-processing involving an in situ reference. The pseudoheterodyne technique can output signals that are proportional to the amplitude and phase of the scattered light. Unfortunately, at each wavelength, the optical phase has an unknown and varying phase offset. Thus the phase versus wavelength (or wavenumber) plot does not closely resemble a conventional absorption spectrum. To convert the phase signal into something approaching an absorption spectrum, it has been necessary to use an in situ reference sample with well-known phase behavior over the wavelength range of interest. The in situ reference sample requirement has led to the need that samples be prepared with an additional known material directly adjacent to the sample of interest. In fact most if not all in situ reference measurements are performed such than a material of interest is sufficiently close to the in situ reference such that the material of interest and the reference material can be imaged in the same field of view of the same AFM image. The in situ reference sample also must have a flat or otherwise well-known phase behavior. This in situ reference requirement has dramatically limited the types of samples that can be successfully measured, as many if not most real world samples do not have a suitable reference material available. Therefore special sample preparation steps are required to prepare a sample with material of interest on a substrate that can serve as a reference material or to prepare the material of interest with an in situ reference sample adjacent to the material of interest.

Further, any errors in either the measured or assumed phase of the in situ reference sample lead directly to errors in the calculated spectrum of an unknown sample. In practice, absorption spectra calculated from prior art s-SNOM measurements have contained distortions in absorption band shapes, offsets in absorption peak positions, and errors in relative absorption peak heights. These errors lead to complications in the interpretation of s-SNOM spectra and discrepancies from the standard spectra known from materials databases. Additional errors may be present in systems such as FIG. 1A, or in other system with similar arrangements. The scattered light from the tip-sample region 110 is interfered with light in the reference arm 134, which may be completely separate from the sample arm of the interferometer 122. This interferometer scheme amplifies the weak tip-scattered light and also enables measurements of the optical phase of the scattered light. The disadvantage of interferometric detection is that it is extremely sensitive to differential changes in the optical path length between the sample arm and reference arm, for example due to temperature or air current fluctuations.

Next we turn to issues of spectroscopic measurements in the prior art using s-SNOM techniques. For many years s-SNOM was primarily an imaging technique, but in recent years it has been possible to collect optical spectra from sub-micron regions of a sample. There have been two basic approaches. In one approach a broadband laser is used to illuminate the sample simultaneously with light from multiple wavelengths. In this case interferometric Fourier transform techniques are used to deconvolve the wavelength dependent scattering to obtain near field spectra. This technique is outlined for example in publications from the Hillenbrand research, for example in Amenabar et al. Nat Commun 4 (2013). This technique requires sophisticated femtosecond lasers which can be expensive, complicated, power limited and have limited spectral coverage.

Alternately, a technique sometimes referred to as "spatiospectral imaging" is employed. In this case a narrow band tunable source, for example a quantum cascade laser is used to collect a series of s-SNOM images at different wavelengths. To obtain spectra from this technique, however, is usually extremely tedious. For example, each s-SNOM image at each center wavelength may take 5-20 minutes to acquire. To acquire even a minimal spectrum at 10 different wavelengths for example would require 50-200 minutes, just to obtain the images. For a more useful spectrum, for example covering 400 cm−1 with 4 cm−1 spectral resolution would require 101 points thus requiring 505-2020 minutes, or 8-33 hours. As such it has been impractical to use the spatio-spectral technique for rapid point spectroscopy, i.e. measuring the absorption spectrum of a single point. The AFM-IR technique, described in U.S. Pat. No. 8,001,830, by comparison does not require an in-situ reference and point spectra can be obtained in around a minute. Some samples are not suitable for measurement by AFM-IR, however, and it is desirable to have a method of obtaining point spectra using the s-SNOM technique on similar time scales.

Definitions

"Interacting a probe with a sample" refers to bringing the probe tip close enough to the surface of a sample such that one or more near field interactions occur, for example the attractive and/or repulsive tip-sample forces, and/or the generation and/or amplification of radiation scattered from an area of the sample in proximity of the probe apex. The interaction can be contact mode, intermittent contact/tapping mode, non-contact mode, pulsed force mode, and/or any lateral modulation mode. The interaction can be constant or as in preferred embodiments, periodic. The periodic interaction may be sinusoidal or any arbitrary periodic waveform. Pulsed force modes and/or fast force curve techniques may also be used to periodically bring the probe to a desired level of interaction with a sample, followed by a hold period, and then a subsequent probe retraction.

"Illuminating" means to direct radiation at an object, for example a surface of a sample, the probe tip, and/or the region of probe-sample interaction. Illumination may preferably include radiation in the infrared wavelength range, but other wavelengths may also be used. Illumination may include any arbitrary configuration of radiation sources, reflecting elements, focusing elements and any other beam steering or conditioning elements. The source of infrared radiation may be one of a large number of sources, including thermal or Globar sources, supercontinuum laser sources, optical parametric oscillators (OPOs), optical parametric generators (OPGs), quantum cascade lasers (QCLs), nanosecond, picosecond and femtosecond laser systems, CO2 lasers, heated cantilever probes or other microscopic heaters, and/or any other source that produces a beam of infrared radiation. The source emits infrared radiation in a preferred embodiment, but it can instead or also emit in other wavelength ranges, for example from ultraviolet to THz.

"Scattering" or "scattered" refers to radiation emitted from a region by a mechanism other than specular reflected light. Scattering can include a variety of mechanisms including elastic scattering, inelastic scattering, fluorescence, Raman scattering, and any other mechanism that involves radiation being emitted from a surface in response to incident radiation (other than simply reflected light).

"Collecting radiation" means to collect radiation at or with a suitable radiation detector, for example at a photodiode, photoconductor or similar detector that converts an radiation into a current, voltage, temperature or other signal that can be measured.

"Near-field selective amplification" refers to one or more techniques that are applied to selectively amplify and/or discriminate light that is scattered from the region of a sample in proximity to the probe apex, while diminishing the relative contribution from radiation scattered from other sources, for example scattered from regions of the sample away from the probe apex, and/or radiation scattered from the shank of the probe tip away from the tip apex and/or the cantilever body. "Near-field selective amplification" can include modulation of the probe-sample distance, time gating of collected radiation, asymmetric interferometric amplification, or frequency domain techniques that select frequency components at frequencies corresponding to higher harmonics of the probe motion.

"Spectrum" refers to a measurement of one or more properties of a sample as a function of wavelength or equivalently (and more commonly) as a function of wavenumber.

"Optical property" refers to an optical property of a sample, including but not limited to index of refraction, absorption coefficient, reflectivity, absorptivity, real and/or imaginary components of the index refraction, real and/or imaginary components of the sample dielectric function and/or any property that is mathematically derivable from one or more of these optical properties.

"In situ reference" is a material and/or sample in close proximity to a sample of interest with a flat and/or known phase dependence over a wavelength range of interest. The sample of interest is typically mounted directly on the in situ reference sample (for example a sample on a gold or silicon substrate) where some portion of the substrate is maintained bare (without a sample of interest covering it). Such samples can facilitate direct comparison between the phase of a known sample with a sample of interest. In situ reference samples are typically made by scratching away a portion of a sample of interest to reveal the underlying substrate or masking a region the substrate when the sample of interest is deposited.

"Background scattering" refers to radiation scattered from regions of the sample away from the probe apex, and/or radiation scattered from the shank of the probe tip away from the tip apex and/or the cantilever body.

"Interference," "Interfering," and "Interferometry" all refer to the coherent superposition of multiple electric field components from two or more sources. When interfering beams reach a detector intensity measured at the detector depends on the complex sum of the real and imaginary electric field components, or equivalently both the amplitude and optical phase of the electric field components. Interferometry is one of the techniques employed to obtain "Near-field selective amplification," as described above.

"Reference beam" refers to an auxiliary optical beam that is interfered with the sample scattered beam at the detector.

"Signal indicative of" refers to a signal that is mathematically related to a property of interest. The signal may be an analog signal, a digital signal, and/or one or more numbers stored in a computer or other digital electronics." The signal may be a voltage, a current, or any other signal that may be readily transduced and recorded. The signal may be mathematically identical to the property being measured, for example explicitly an absolute phase signal or an absorption coefficient. It may also be a signal that is mathematically related to one or more properties of interest, for example including linear or other scaling, offsets, inversion, or even complex mathematical manipulations.

A "transimpedance amplifier" refers to an electronic device that converts current to a voltage through active amplification. The most common transimpedance amplifier are circuits built with operational amplifiers and feedback resistors, but equivalent circuits can be built with discrete transistors. The transimpedance amplifiers can have fixed gain, a limited set of fixed gain values and/or variable gain. Similarly, the bandwidth can be fixed or adjustable. The transimpedance amplifier may include a biasing circuit provide bias to the photodetector.

"Tunable narrow band radiation source" refers to a source of radiation that emits radiation with an adjustable center wavelength, yet with a full width half maximum emission bandwidth of less than 8 $cm^{-1}$ or preferably less than 1 $cm^{-1}$. An example of a tunable narrowband source is a quantum cascade laser (QCL) and/or an array of quantum cascade lasers. Other tunable narrowband radiation sources may include optical parametric oscillators and other laser technology if they include tenability of the center wavelength and the narrow band emission mentioned above.

SUMMARY OF THE INVENTION

Therefore, the object of the current invention is to overcome the limitations of the prior art in IR s-SNOM. Specifically, the current invention enables efficient, high sensitivity measurements of the amplitude and phase of the near field tip scattered light. It also enables high speed demodulation of the near field signal in support of high speed nanoscale spectroscopy and chemical imaging. The current invention also enables rapid and accurate calculations of near field phase while eliminating the need for an in situ reference sample. In some embodiments, errors due to interferometer path length and physical separation are reduced. In other embodiments, appropriate samples of interest are mounted on or in close proximity to a reference region with constant or known properties over the wavelength range of interest, while still enabling a rapid and efficient method for producing reflection/absorption spectra over a range of wavelengths. In some embodiments, the spectra comprise IR absorption spectra which can enable chemical analysis and identification.

BRIEF DESCRIPTION OF THE DRAWINGS

The invention will be better understood by referring to the following figures.

FIGS. 4A, 4B, 4C, and 4D show an illustration of the improvement in amplitude and phase errors under the current invention.

FIGS. 9A, 9B, 9C, and 9D illustrate the results of the steps of the method shown in FIG. 8.

DETAILED DESCRIPTION OF THE INVENTION

Figure 2:
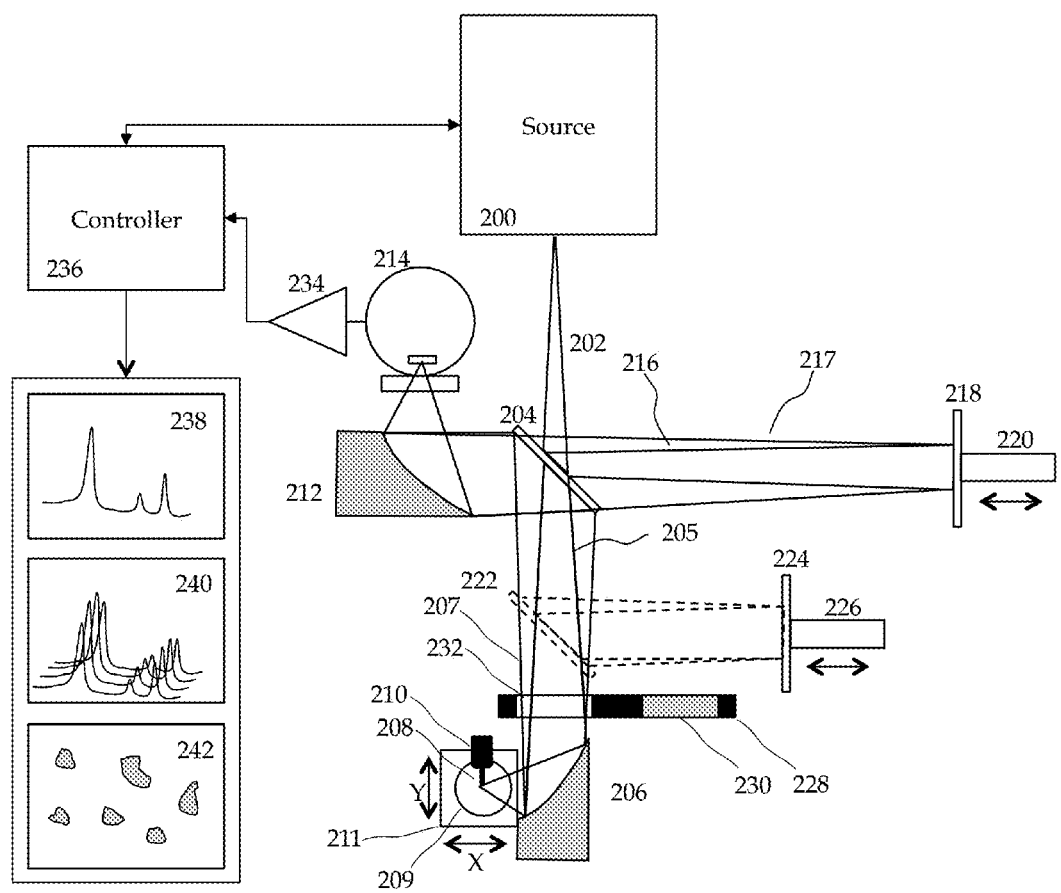
FIG. 2 shows a simplified schematic diagram of one embodiment of the current invention.

FIG. 2 shows a simplified schematic of an embodiment of the current invention. Infrared light 202 is emitted from source 200 towards a beam splitter 204. In FIG. 2, the light 202 is shown as diverging, but it may also be substantially collimated. Light 205 that passes through the beam splitter continues towards a focusing optic 206 that focuses the infrared light onto a sample 209 in the vicinity of the end 208 of a probe 210 of a probe microscope. (FIG. 2 shows a top view looking down on a sample and a cantilever probe—the probe tip and tip apex are not illustrated in this view.) Light scattered from the tip and sample is collected by collection optics. In the simplest implementation the collection optics are the same as focusing optics 206, but alternate and/or additional collection optics can be used instead. Light 207 collected from the collection optic is returned to the beam splitter 204 where it is focused via another focusing optic 212 onto the surface of an infrared detector 214.

A portion 216 of the incident light beam 202 is diverted at the beam splitter 204 towards a reference mirror 218. The light 217 reflected from reference mirror 218 is directed back through the beam splitter and along the same path as the tip/sample scattered beam, focused by focusing optic 212 onto the detector 214. The light in beam 217 is referred to as a "reference beam." In this manner light from the reference arm is interfered with light scattered from the tip and sample. Actuator 220 is used to rapidly adjust the optical path length of the reference arm, thus adjusting optical phase of light reflected from the reference arm. In one embodiment, the actuator 220 is periodically moved λ/8, where λ is the center wavelength of the incident radiation. The actuator may be a piezoelectric device, a flexure-guided actuator, and/or an actuator employing electrostatic, magnetic, voice coil, electrostrictive or other actuation mechanisms. It may also be a precision linear motor or an intertial drive mechanism or any other mechanism that can move accurately on the scale of fractions of a wavelength. The λ/8 motion induces a total path length difference λ/4 (λ/8 both coming and going), resulting in a 90° optical phase shift. Measuring the detector signal at two phases 90° allows calculation of both the optical amplitude and the optical phase of the tip/sample scattered light. Specifically, if the detector signal is measured at two optical phases 90° apart, the amplitude A and phase φ can be calculated by:

$$A = \sqrt{I_0^2 + I_{90}^2}, \phi = \arctan\left(\frac{I_{90}}{I_0}\right) + \phi_0$$

where I0 and I90 are the detector intensities at a 90° phase shift and φ is an arbitrary constant (discussed later associated with FIGS. 8 & 9).

Figure 1:
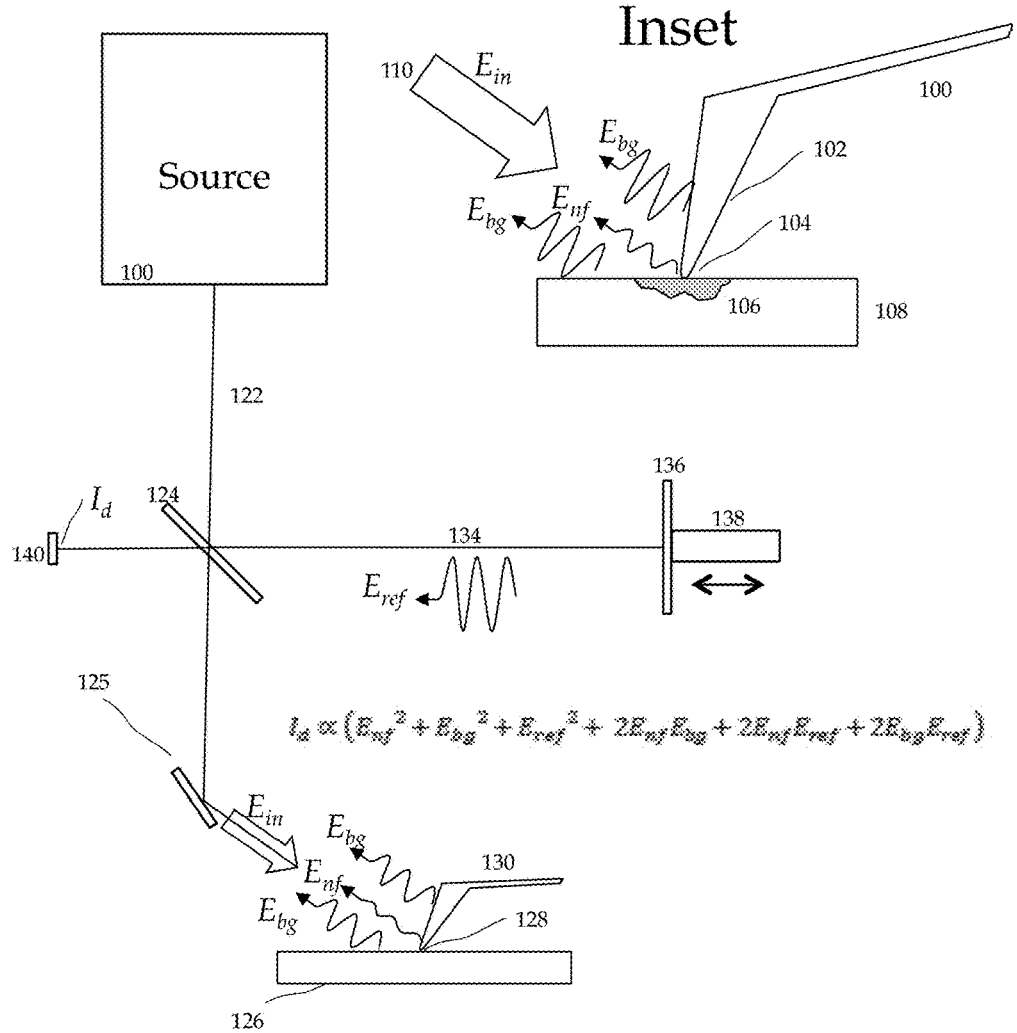
FIGS. 1A and 1B shows a simplified schematic diagram of scattering Scanning Near Field Microscopy (s-SNOM) under the prior art.

Referring back to FIG. 1b, the light scattered from the tip/sample contains two electric field terms. The field scattered from the tip apex 104 and a portion of region 106 of the sample interacting with the tip apex is indicated by Enf and this is the signal of interest. Background scattered radiation from other regions of the probe and sample is characterized by electric field strength Ebg. Note that these are both complex quantities and generally have an unknown phase offset. In general $|Ebg|\gg|Enf|$. This is due to the fact that the illuminated area (i.e. the focused spot size) is many orders of magnitude larger than the tip apex. Thus the background scattered light often dwarfs the amount of light scattered from the tip apex region. (In some cases of extremely efficient tip-enhancement and/or very small background scattering, the near field signal Enf can be larger than the background.)

Referring back to FIG. 2, interference between the reference arm light 217 the tip/sample scattered light also provides amplified detection of the tip/sample scattered light. The light intensity at the detector Id is proportional to $|Etot|^2$, where Etot is the complex sum of the light from the near field scattering, Enf, the background scattered light Ebg and the reference arm light Eref that interferes with the scattered light at the detector. Thus:

$$I_d \propto (E_{nf}^2 + E_{bg}^2 + E_{ref}^2 + 2E_{nf}E_{bg} + 2E_{nf}E_{ref} + 2E_{bg}E_{ref})$$

The amplification of the tip/sample scattered light comes from the cross terms EnfEref and EnfEbg. In the prior art, there has been a competition between these two terms. The amplitude and phase of Ebg are generally unknown and can vary over a surface. As such, if not corrected, this cross term can cause significant errors in optical amplitude and phase measurements of the signal of interest Enf. The prior pseudoheterodyne techniques have attempted to separate out the background cross term from the reference cross term using sinusoidal modulation of the reference arm and then separating the Eref and Ebg cross terms in frequency space, as illustrated in FIG. 3. The current invention can avoid the need to modulate the reference arm phase by ensuring that Eref $\gg$ Ebg, such that the dominant interferometric amplification is performed via the Eref term. Separately, the current invention can employ the simpler frequency separation techniques of the prior art homodyne technique to discriminate between the EnfEref and EbgEref terms. This is achieved by taking advantage of the much steeper nonlinear dependence with tip-sample separation of the near field component versus the background component. FIGS. 10A, 10B, 10C, and 10D show illustrations of the relative distance dependence of the background (10A) and near field (10B) components. The background signal varies slowly with tip-sample separation (the signal strength may actually increase or decrease based on the optical phase). The near field signal, on the other hand, increases very strongly at small tip-sample separations. When the tip is periodically interacted with the sample (e.g. oscillated in tapping mode), the resulting frequency dependent amplitudes are illustrated schematically in FIGS. 10C and 10D. The background signal Ebg (10C) has components primarily at the cantilever fundamental and the 1st harmonic, with negligible contributions at higher frequency. The near field component, Enf (10D), by comparison has a very large number of harmonic components due to the large non-linearity.

If the tip is oscillated at an angular frequency $\omega$, the tip scattered light is proportional to:

$$E_{nf} \propto E_0 \sum_{n=0}^{\infty} a_n e^{in\omega t}$$

The background scattered light is proportional to $$E_{bg} \propto E_0 \sum_{n=0}^{\infty} b_n e^{in\omega t + \varphi}$$

Figure 10A:
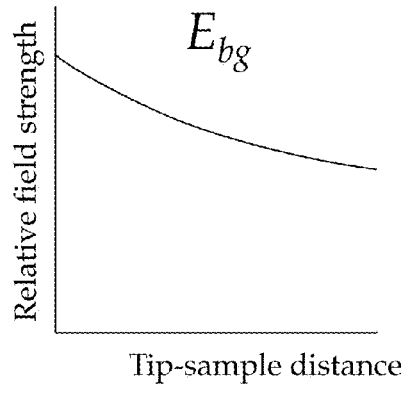
FIGS. 10A, 10B, 10C, and 10D illustrate the difference between the near-field scattered radiation and the background scattered radiation as a function of tip-sample separation and frequency.
Figure 10C:
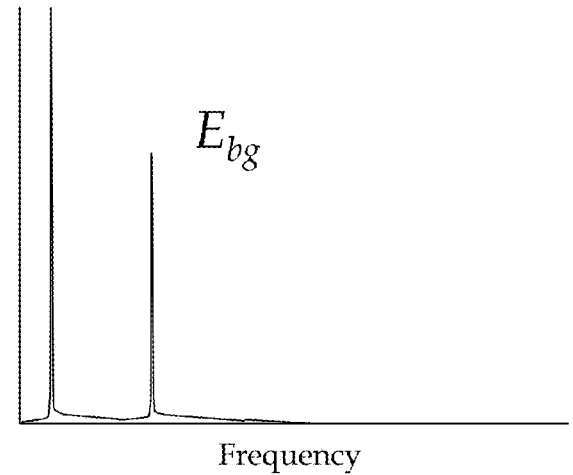
Figure 10B:
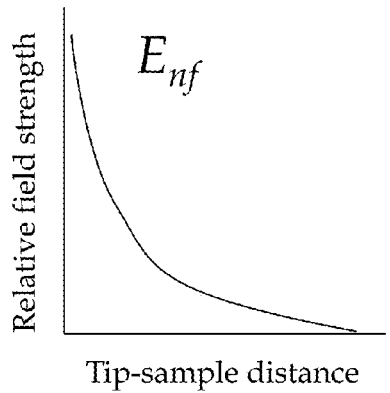

$b_1$, $b_2$ are significant, but for $n \geq 3$, $b_n$ is negligible, as shown in FIG. 10C. The voltage at the detector is proportional to:

$$I_d \propto (E_{nf} + E_{bg} + E_{ref})^2$$

Expanding the terms, we see the detector signal, including key cross-terms $$I_d \propto (E_{nf}^2 + E_{bg}^2 + E_{ref}^2 + 2E_{nf}E_{bg} + 2E_{nf}E_{ref} + 2E_{bg}E_{ref})$$

Considering the scattered light, $E_{nf}$, the component a1 is largest, but is hard to discriminate the near field scatter light $E_{nf}$ from background scattered light $E_{bg}$ that also is modulated at $\omega$. As such, demodulation at $n \geq 3$ is commonly used. It is also desirable to obtain amplitude and phase info separately. So in pseudoheterodyne the phase of $E_{ref}$ is modulated at another frequency such that the cross term is modulated at a different frequency. But this has a significant disadvantage as it spreads out energy from $E_{nf}$ to other sidebands, reducing the signal to noise ratio and increasing measurement time.

The current invention employs near-field selective amplification to discriminate the near field scattered radiation from background scattered radiation. The current invention avoids these problems with the pseudoheterodyne approach (U.S. Pat. No. 7,738,115) and also overcomes the large amplitude and phase error limitations of the earlier homodyne prior art described by Taubner (Journal of Microscopy, Vol. 210, Pt 3 Jun. 2003, pp. 311-314).

Figure 3A:
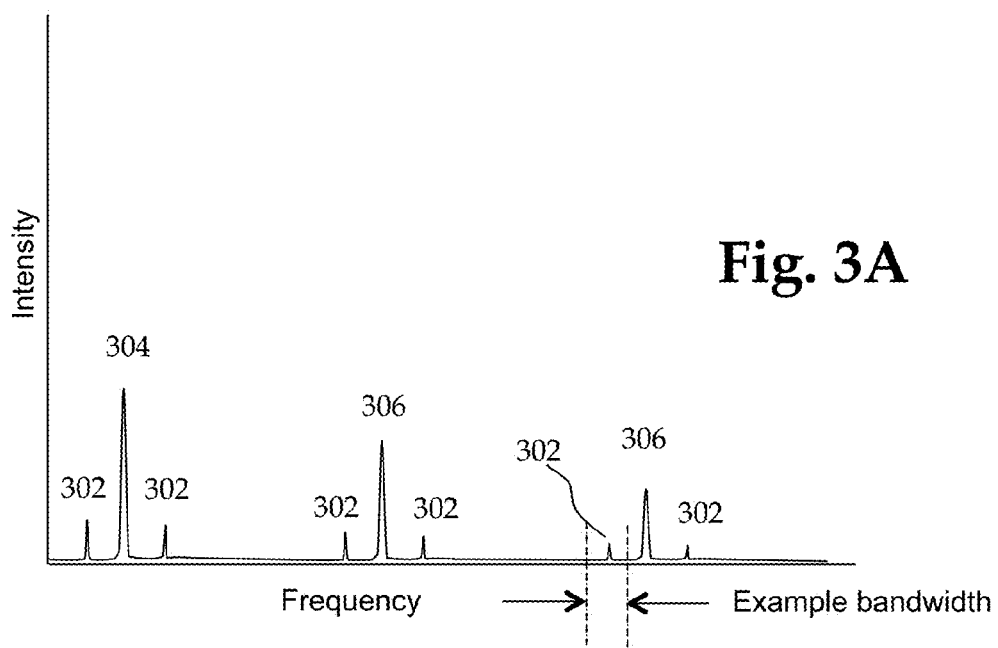
FIGS. 3A and 3B show an illustration comparing demodulation bandwidth requirements of the prior art pseudoheterodyne approach versus the current invention.
Figure 3B:
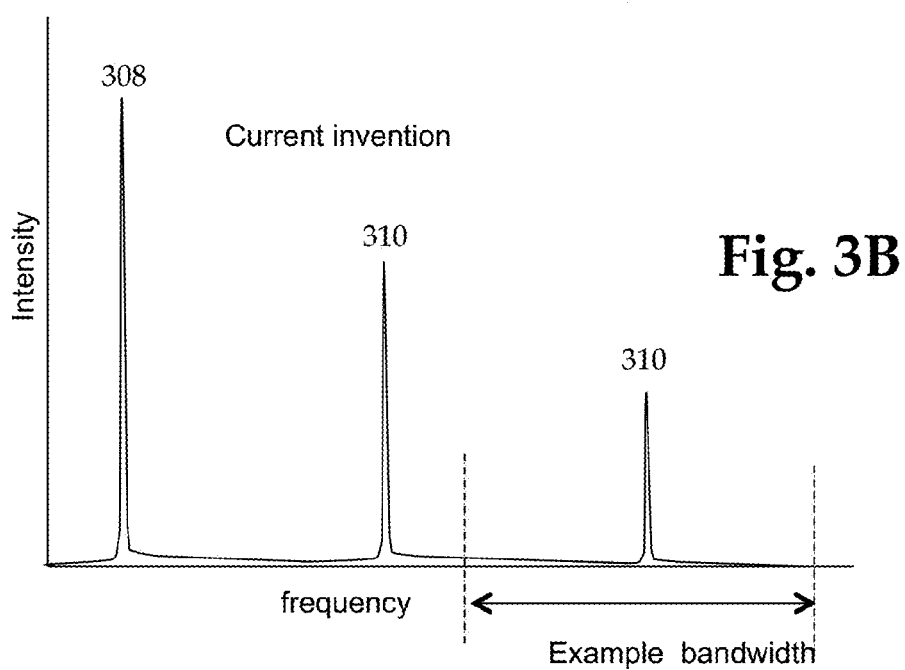

FIGS. 3A and 3B demonstrate how the current invention employs a more robust approach than homodyne prior art to discriminate near field and background signals. FIGS. 3A and 3B show the amplitude error and phase error respectively for the homodyne prior art (solid lines) versus the current invention (dashed lines). The amplitude and phase errors for the homodyne approach were calculated using the equations in the background section of U.S. Pat. No. 7,738,115 when discussing the prior art homodyne approach.

To achieve these reductions in amplitude and phase error the current invention, in one embodiment, carefully arranges the relative field strengths such that Eref $\gg$ Ebg. In this case, it is possible to neglect the cross term EnfEbg since the EnfEref cross term is so much larger. FIG. 4C shows the dependence of the amplitude and phase errors on the ratio of Eref:Ebg. The prior art homodyne technique was limited to Eref:Ebg of 3-10, resulting in amplitude errors in excess of 40% and phase errors in excess of 25°. By contrast, the current invention achieves Eref:Ebg of >20, or preferably more than 50, and more than 150 in some embodiments. With an Eref:Ebg ratio of 150, the amplitude error is less than 1% (FIG. 4A) versus 28% under typical conditions as described in U.S. Pat. No. 7,738,115 (see Col 2, line 64-Col 3 line 4) Additionally, the phase error can be 0.5° or less (FIG. 3B) under the current invention, versus 19° described in the aforementioned patent. FIG. 4D tabulates the improvement in amplitude and phase error versus a homodyne prior art value of Eref:Ebg=5, described as typical in the '115 patent.

The relationship between amplitude and phase errors versus the Eref:Ebg ratio is illustrated in FIGS. 4C and 4D. The relationship is roughly an inverse law relationship, i.e., the amplitude and phase errors are roughly proportional to 1/(Eref:Ebg). The prior art has been restricted to Eref:Ebg, in the range of 3-10, contributing to amplitude errors of up to 47% and phase errors of up to 28°. Under the current invention, the inventors can achieve Eref:Ebg ratios of >20, or preferable more than 50, or even more preferably above 150. Even with a Eref:Ebg ratio of 20, the amplitude error can be ~7%, already 4× better than the typical prior art value. At Eref:Ebg=50, the amplitude error is 2.8%, 10× better than the prior art. And at Eref:Ebg=150, the amplitude error is 0.9%, roughly 30× better than the prior art. Similar improvements are seen in the phase error with roughly 4×, 10× and 30× reductions in the phase error with Eref:Ebg=20, 50, and 150 respectively. This relationship between amplitude/phase errors and the Eref:Ebg ratio was understood by Ocelic and Hillenbrand and discussed in the U.S. Pat. No. 7,738,115 as a motivation for their use of pseudoheterodyne techniques to attempt to overcome the problem. As mentioned previously and discussed elsewhere, the implementation of pseudoheterodyne leads to several performance limitations.

The current inventors have overcome the prior art limits on the Eref:Ebg ratio and thus eliminated the need to perform more complex pseudoheterodyne measurements. The inventors have overcome the prior art limits using three linked steps. First, the inventors have employed linear response mercury cadmium telluride detectors that can achieve a linear response regime at more than 30× higher intensity that detectors used in the prior art. Second, the inventors carefully adjust and/or attenuate the strength of the reference beam so that the intensity from the Eref2 term almost saturates the detector. Third, and somewhat counter intuitively, the inventors optionally attenuate the light in the sample arm to suppress the background scattered light, thus improving the Eref:Ebg ratio.

Returning to FIG. 2, the source of infrared radiation 200 may be one of a large number of sources, including thermal or Globar sources, supercontinuum laser sources, optical parametric oscillators (OPOs), optical parametric generators (OPGs), quantum cascade lasers (QCLs), nanosecond, picosecond and femtosecond laser systems, CO2 lasers, heated cantilever probes or other microscopic heaters, and/or any other source that produces a beam of infrared radiation. Source 200 can alternately or additionally be a source of other wavelengths, for example from ultraviolet to terahertz radiation. Source 200 preferentially has high amplitude and phase stability to provide consistent amplification through the ErefEnf term. In some cases, it can be beneficial to take extra steps to stabilize the source energy, for example through dynamic adjustments of the laser cavity, limiting the bandwidth on the drive current, controlling the temperature of the source or other techniques that can maximize the stability of the Eref term.

Controller 236 can dynamically adjust the output power of radiation source 200 to maximize intensity at the detector 214 such that the intensity is near the limit of the linear range of the detector. Variable attenuator 228 can dynamically adjust the fraction of light that is incident on the sample and simultaneously attenuate the background scattered light Ebg. In one embodiment, variable attenuator 228 is a filter wheel with various neutral density filters 230 at a plurality of locations in the filter wheel. The neutral density filters can be made from metal meshes so that there is no wavelength dependent refraction from dispersive optical components with finite thickness. Neutral density filters may also be made from IR transparent materials, for example germanium, zinc selenide or other materials with suitable metal and/or dielectric coatings. Any other attenuating optical element may be used in place of or in addition to filters, including but not limited to iris diaphragms, polarizing optics or other attenuating devices. Additionally, one or more location 232 in the filter wheel may be empty to be used in the case of weak scattering from the sample or small background scatter that does not require attenuation. Additional filter wheels can be placed in the reference arm and/or the source arm and/or detector arm (not shown).

The infrared detector 214 generates a photocurrent that is amplified by amplifier 234. Amplifier 234 may be a transimpedance amplifier that provides a large linear detection regime and maintains a small potential across the photodiode. (This is one approach to achieve a much larger linear range than a photoconductive detector thus enabling higher intensity reference beams and large Eref:Ebg ratios.) Alternative suitable detectors may be used for other wavelengths than infrared.

Figure 10D:
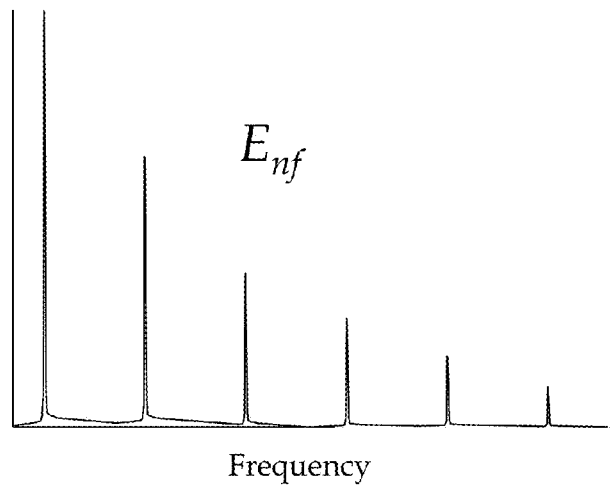

The probe end 208 is oscillated or otherwise modulated at one or more frequencies ωi, for example by exciting one or more mechanical resonances of a cantilever probe. The current invention then also employs frequency space separation to achieve near-field selective amplification. The background signal Ebg generally only has significant AC components at the 1ω and 2ω frequencies, where ω is the frequency of interaction of the probe with the sample (e.g. an oscillation frequency). At n≥3, the near field signal dominates the background signal because the near field signal has a much higher nonlinearity (more significant increase at shorter tip-sample distances). At frequencies no where n≥3, the near field signal dominates, i.e. Enf>>Ebg, as illustrated in FIG. 10C-D.

The controller 236 can include demodulation capabilities to extract the component of the signals from detector 214 and amplifier 234 at the oscillation frequencies and their harmonics. The controller may comprise multiple separate components, for example a piezo amplifier, a lock-in amplifier, data acquisition/control device, and a computer. Alternately, all controller functions may be contained within a single integrated device. Specifically, the demodulation capability can extract oscillatory components of the detector signal at nωi, where n is an integer. The demodulator may be a conventional lock-in amplifier, or alternately a multifrequency lock-in from Zurich Instruments. In a preferred embodiment the lock-in is a digital lock-in amplifier that acquires analog measurements from the detector/amplifier and then performs discrete digital calculations to determine the oscillatory components at one or more integer multiples of an oscillation frequency. The demodulator can be implemented on digital electronics, for example using field programmable gate array (FPGA), digital signal processor (DSP) or similar technologies. The demodulation can also be performed rapidly on a personal computer by calculating discrete Fourier sums that correspond to a response at a desired frequency. The demodulator generally produces two or more terms for each demodulation frequency, for example magnitude and phase or in-phase (X) and quadrature (Y). Note that the probe end may also be interacted with the sample with non-sinusoidal modulation and demodulation can use alternative basis functions, for example wavelets, Bessel function, or other functions selected to model the nonlinear tip-sample distance dependence of the near field scattered radiation.

The demodulator can also analyze any number of higher harmonic amplitudes, excluding components at the cantilever's fundamental oscillation frequency. For example a Fourier transform can be applied to extract any number of Fourier components at one or more frequencies corresponding to harmonics of the cantilever motion. Note also, it is not necessary to calculate an entire Fourier transform. It is possible to discretely calculate the response at any desired frequency with an appropriate Fourier sum, i.e. calculating the Fourier component at a specific desired frequency. Since the cantilever motion frequency is well known and determined in one embodiment by the SPM controller, the desired Fourier components can be calculated very quickly at well specified frequencies. It is also possible to sum the amplitudes at multiple Fourier components, for example at the 3rd-8th harmonics of the cantilever motion. One way to calculate the total intensity from a specified number of higher harmonics is to employ a circuit and/or a computation to determine total harmonic distortion (THD). Total harmonic distortion calculations or THD analyzers usually sum the harmonic component for some specified number of harmonics above the fundamental oscillation frequency. (In some cases it can be desirable to begin the THD sum starting at the third harmonic thus providing better rejection of the background scattered light that can have a component at the 2nd harmonic.)

In one embodiment, it is possible to perform demodulation at very high rates. For example it is possible to achieve high quality near field scattering images in <5 minutes, similar to conventional AFM imaging speed. It is also possible to achieve high quality near field scattering spectra in less than 1 minute. The reason is that it is possible to demodulate directly at a cantilever resonance or a higher harmonic of that resonance, rather than at a sideband as required for pseudoheterodyne techniques. FIG. 3 illustrates this issue. Under the pseudoheterodyne technique, the reference arm modulation introduces side bands 302 around the cantilever oscillation frequency 304 and its harmonics 306. To demodulate the amplitude of a sideband 302, it is necessary to employ a narrow bandwidth detection technique to avoid contamination from the often much larger signal at the adjacent harmonic frequency 306. An example bandwidth that would isolate a single sideband is shown schematically with dashed lines in FIG. 3A.

By contrast, the current invention need not apply sinusoidal modulation to the reference mirror and as such need not distribute energy to any sidebands. The demodulated peaks at the cantilever resonance (308) and higher harmonics (310) are much more widely separated, as indicated in FIG. 3B. Thus the current invention has one advantage in that it can apply wide bandwidth demodulation thus requiring very short integration times. In addition, with the larger values of Eref:Ebg it is possible to achieve much large asymmetric amplification of the near field scattered signal Enf. Thus the amplitudes of the demodulated response are much larger than the pseudoheterodyne approach, but also larger than the demodulated peak heights in conventional homodyne approaches. With higher signal to noise ratios versus the prior art homodyne approach (constrained by smaller Eref:Ebg) it is possible to take advantage of these increased bandwidths and short integration times. The shorter integration times dramatically increase measurement speed and improve the throughput of the instrument.

Figure 11A:
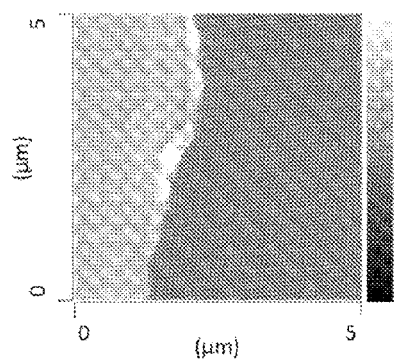
FIGS. 11A and 11B show a topography image and a near-field scattered radiation image of the same region of a sample.
Figure 11B:
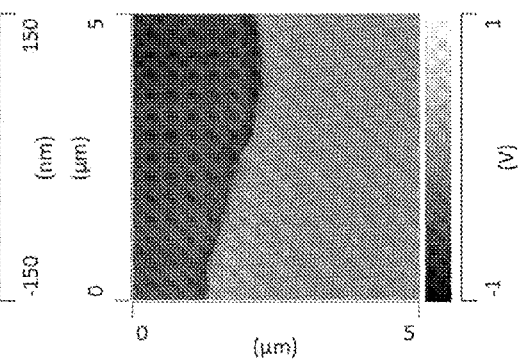

For example, if it is desired to demodulate at the 3rd harmonic of a fundamental cantilever resonance at 80 kHz, the separation between bands is 80 kHz. So when the signal to noise ratio permits, a demodulation bandwidth up to ~150 kHz can be used while avoiding contribution from other frequency bands. (The specific bandwidth and potential crosstalk from neighboring bands depends on demodulation factors like the properties of any window function used in the demodulation.) Because the demodulation bandwidth can be very fast, the scattered radiation can be measured very quickly. For example, a bandwidth of 100 kHz allows one measurement point every 10 μsec. With sufficient signal to noise, a 200 point spectrum can be obtained in as little time as 2000 μsec. But even with a narrower bandwidth to provide more noise rejection, for example 2 kHz bandwidth can still achieve a 200 point spectrum in as little as 0.1 sec. To achieve these spectrum measurement times it is desirable to tune the IR source continuously, rather than in a step/settle/measure scheme. Even with step/settle/measure scheme it is possible to achieve a spectrum in less than a minute, for example with 200 points and 0.25 seconds of step/settle time. Similarly, a single wavelength scattering image with a pixel resolution of 200×200 points can achieved obtained in as little as 20 seconds with a 2 kHz demodulation bandwidth. FIGS. 11A and B show an example measurement of 200×200 points acquired with a bandwidth of 1.2 kHz and at a line rate of 0.2 seconds per line, corresponding to a bidirectional image time of 40 seconds. FIG. 11A shows a topographic image of an interface between gold and silicon. FIG. 11B shows an image indicative of near-field scattered radiation under the current invention of the same region. In addition to the bandwidth benefits, the direct demodulation at one or more major harmonic of the cantilever motion (not a side band) maintains much higher signal to noise, whereas pseudoheterodyne techniques move only a portion of the signal into sidebands, thus reducing signal to noise ratio.

As mentioned previously, the scattering and demodulation measurements are preferably performed at two position of the reference mirror 218 (FIG. 2), corresponding to two optical path lengths separated by 90° of optical phase. Measuring the demodulator outputs at two positions of the reference mirror with 90° of optical phase difference enables separate computation of the optical amplitude and optical phase of the scattered light. These measurements of optical amplitude and phase can be used to extract the optical properties of submicron regions of a sample surface. In particular, it is possible to calculate a near field absorption spectrum 238 from these measurements. The absorption spectrum primarily comes from the optical phase signal, a measure of dissipation, although it may be necessary to correct the measured optical phase due to wavelength dependent dispersive effects (i.e. changes in the real index of refraction).

The sample 209 and/or probe 210 may be translated relative to each other, for example with an XY scanner 211. This enables measurements of the spatial distribution of optical properties of the sample, with sub-micron spatial resolution. In one example, absorption spectra 238 or other optical properties can be mapped at a plurality of points 240 on a sample to create spatially resolved profiles of the optical properties of the sample. Alternately, the optical properties can be mapped at a plurality of regularly spaced XY points to create a chemical map 242 of the sample surface. In one embodiment, each pixel of the chemical map comprises measurements at a plurality of incident wavelengths. In other embodiments, the chemical map represents a scattering signal measured at a plurality of XY sample positions, but at a single wavelength.

Figure 5:
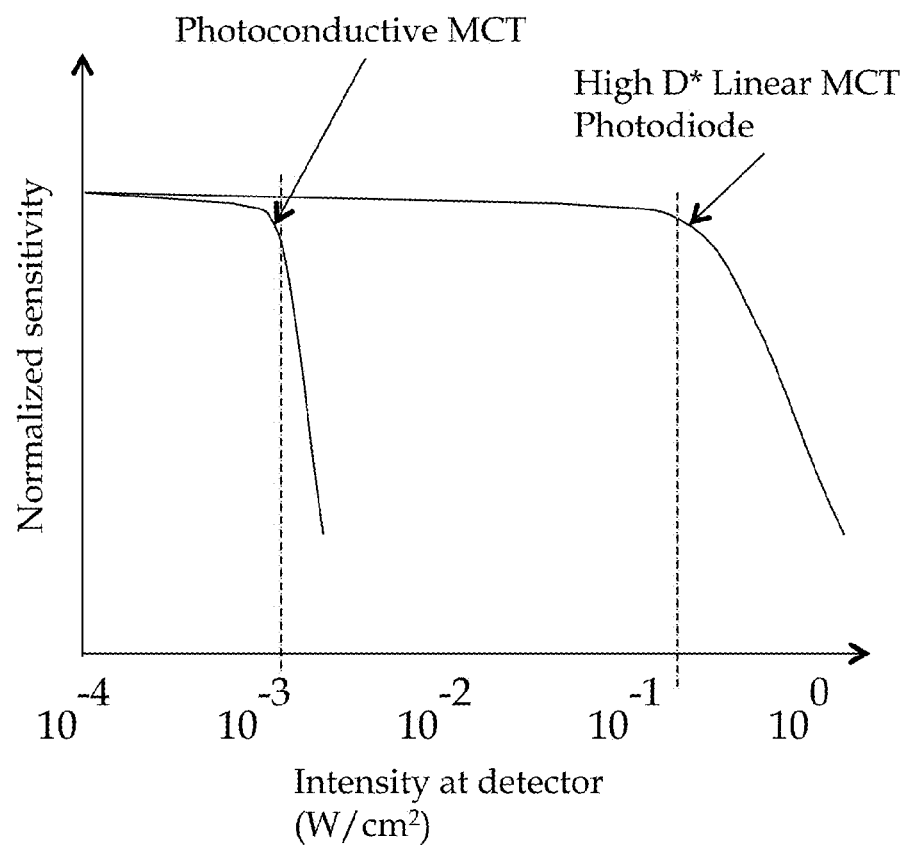
FIG. 5 compares the linear range of infrared detectors used in the prior art versus one embodiment of the current invention.

Turning to FIG. 5, we discuss briefly the selection of an infrared detector. Most if not all prior art measurements in IR-s-SNOM have been performed with photoconductive mercury cadmium telluride (MCT) detectors. For example, Hillenbrand's group apparently typically uses a Judson Teledyne J15D12-M204-5050U photoconductive MCT detector (see Nature Materials, Vol 10, May 2011, p. 352, DOI: 10.1038/NMAT3006). The current inventors have built their s-SNOM with a "High D* Linear MCT Photodiode," rather than a photoconductive MCT. As illustrated schematically in FIG. 5, the linear MCT photodiodes have a much larger dynamic range. While a photoconductive MCT may reach saturation around $10-3$ W/cm2, the linear MCT photodiodes can provide a substantially linear response operate out to 0.1 to 1 W/cm2, depending on the transimpedance gain and bias conditions. This increase in dynamic range enables much more efficient asymmetric amplification of the near field signal. The reason is that the signal we are generally interested in results from the cross-term ErefEnf, i.e. the amplification of the near field signal by the reference arm field strength. The value of the Eref is limited in general by the dynamic range of the IR detector, specifically due to the Eref2 term. A low limit on the maximum detector intensity for photoconductive MCTs constrains the maximum value of Eref2 and hence the maximum amplification of the Enf term. By switching to a high D* linear MCT photodiode, Eref2 can be orders of magnitude larger, resulting in much higher Eref:Ebg ratios, enabling the improvement in amplitude and phase errors discussed above. One suitable linear MCT photodiode is for example model KLD-0-0.5-J1-3/11/DC from Kolmar. Other models can also be suitable depending on bandwidth requirements and focused spot size. Another alternative is thermoelectrically cooled MCT detectors which have saturation up to 1 W/cm2, up to 100× better than liquid nitrogen cooled. These detectors have much higher noise floors and may only be suitable with higher scattered intensities that are well above the detector noise floor. To achieve the highest Eref:Ebg ratios it is generally desirable to arrange the Eref term such that the total intensity at the detector (dominated by Eref2) is in the range between 10% and 90% of the detector's linear range. It is also possible to work with intensities slightly above the linear range limit where the increase in amplification is still greater than the decrease in sensitivity.

Figure 6:
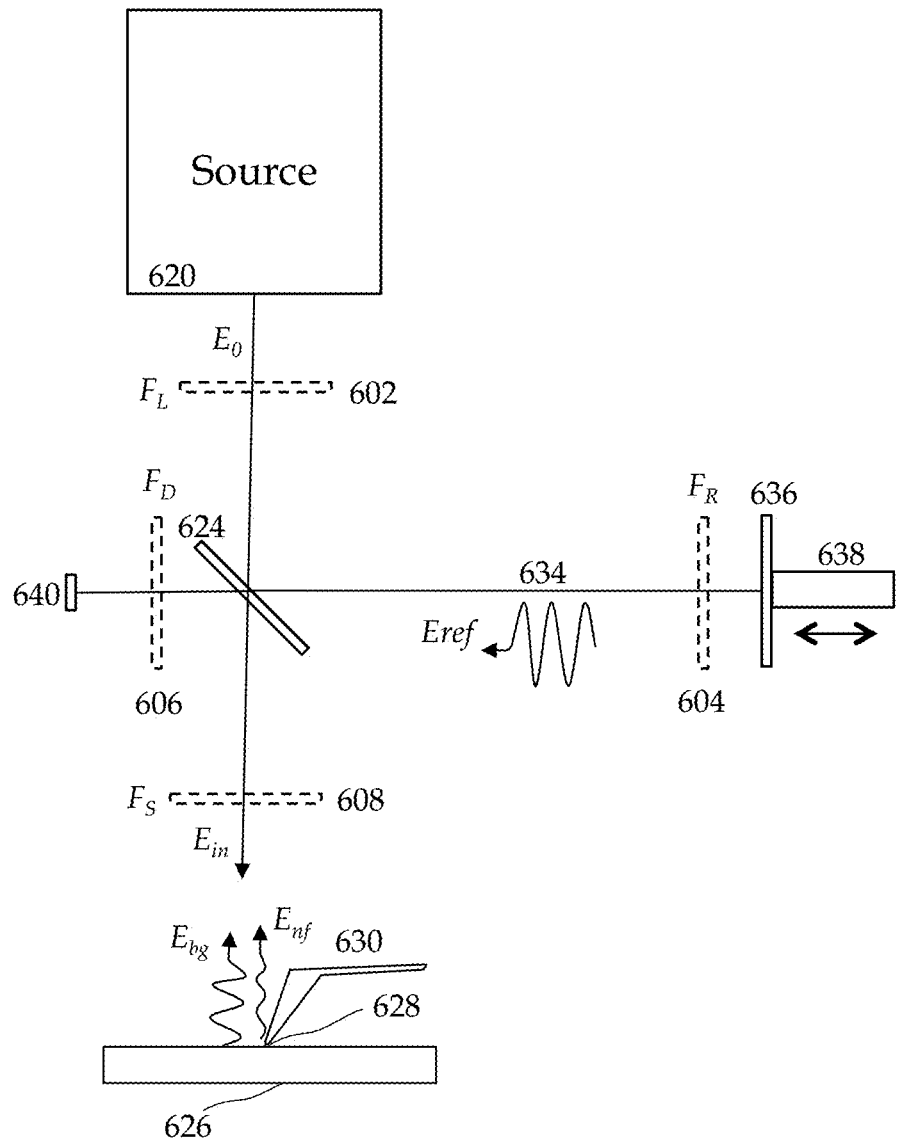
FIG. 6 is a simplified schematic diagram showing filter positions in one embodiment of the current invention to achieve high levels of discrimination between near-field and background signals.

Turning to FIG. 6, we discuss next optimal attenuation of the interferometer beam components, including the counterintuitive step of placing a filter in the sample arm. FIG. 6 shows a simplified version of the interferometric detection used in s-SNOM, except that a filter has been placed in each arm of the interferometer, e.g. a filter 602 in the laser source arm, a filter 604 in the reference arm, a filter 606 in the detector arm and a filter 608 in the sample arm. The transmission coefficients of each of these filters are given by $F_L$, $F_R$, $F_D$, and $F_S$, respectively. As before, light from source 620 is directed to beam splitter 624 where it is divided into two paths, on to reference mirror 636 and one towards probe tip 628 and sample 626. The light scattered from the tip apex region Enf and the background light scattered Ebg recombine with the reference arm light Eref at the detector 640. By tracing each of the beams through each filter and the beam splitter, we can determine the relative field strengths at the detector in the presence of the filters.

The strength of the electric field from the near field scattered light at the detector is given by:

$$E_{nf} = \alpha_{nf} E_0 \sqrt{F_L F_D F_S^2 RT}$$

where R and T are the reflection and transmission coefficients of beam splitter 624, $\alpha_{nf}$ is the near field scattering coefficient and $E_0$ is the original electric field intensity from the source 620. Similarly, the background scattered light is given by:

$$E_{bg} = \alpha_{bg} E_0 \sqrt{F_L F_D F_S^2 RT}$$

where $\alpha_{bg}$ is the background scattering coefficient.

The electric field from the reference arm is given by:

$$E_{ref} = E_0 \sqrt{F_L F_D F_R^2 RT}$$

The signal term that we are interested in is the cross term $E_{ref}E_{nf}$, whereas the unwanted background term is $E_{bg}E_{nf}$. Therefore, the signal to background ratio is given by:

$$\frac{S}{B} = \frac{E_{ref}E_{nf}}{E_{bg}E_{nf}} = \frac{E_{ref}}{E_{bg}} = \frac{E_0\sqrt{F_L F_D F_R^2 RT}}{\alpha_{bg} E_0 \sqrt{F_L F_D F_S^2 RT}} = \frac{F_R}{\alpha_{bg} F_S}$$

Interestingly, this points out that the filter 606 in the detector arm and the filter in the source arm 602 have no impact on the signal to background ratio (as long as the detector operates in a linear regime). Instead to maximize the signal to background we wish to maximize the FR term and minimize the FS term. The filter can have transmission coefficients between 0 and 1, so we may choose FR=1, its maximum value. Thus to increase the signal to background, we want to make FS as small as practical. This seems counterintuitive, as a filter 608 in the sample arm also attenuates the signal of interest Enf. With the asymmetric interferometer, however, it is possible to substantially amplify the near field scattered light Enf through the cross term ErefEnf. In the prior art it had not been possible to make Eref very large due to limits on the linear response regime of the detectors used. But with the detectors used in the current invention, it is possible to use much higher values of Eref and hence smaller values of Enf to get the same overall signal intensity.

Figure 7A:
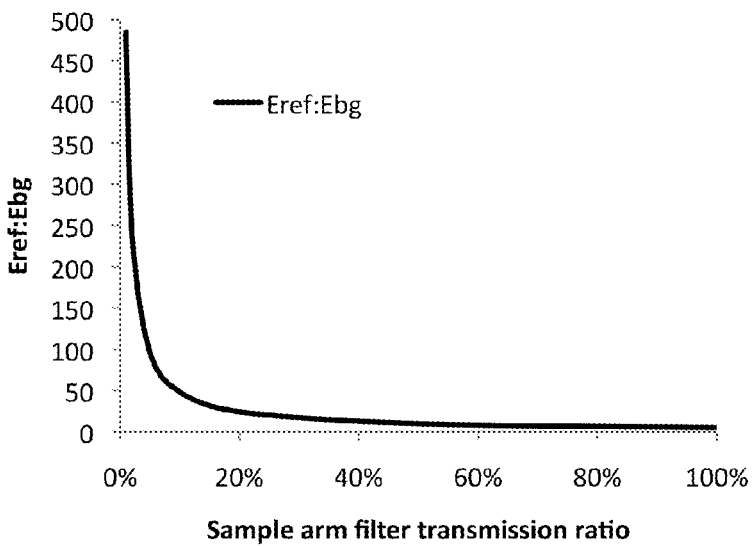
FIGS. 7A and 7B show an illustration of the ratio between reference intensity to background scattered light and amplitude/phase errors as a function of sample arm filter transmission ratio.
Figure 7B:
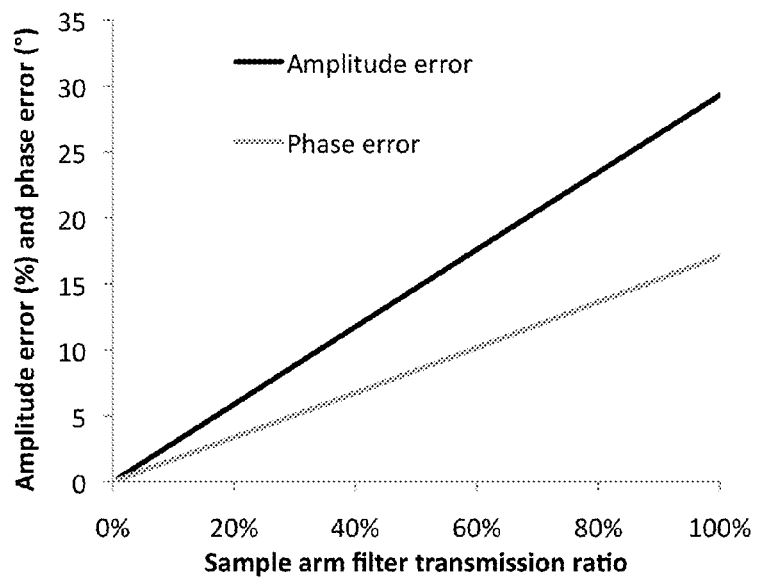

FIG. 7A shows an example relationship between the sample arm filter transmission coefficient and the ratio Eref:Ebg. The exact relationship will depend on a variety of experimental and sample parameters, but this figure shows the basic relationship. In this example, using parameters similar to those commonly used in s-SNOM, it is possible it is possible to achieve an Eref:Ebg value of 50× with a filter with a transmission of 10%. The corresponding amplitude and phase errors are shown in FIG. 7B. Again with a sample arm transmission coefficient of 10%, the amplitude error is less than 3% and the phase error is less than 2°. With currently available laser sources, especially when focused to a diffraction limited spot, it is possible to have sufficient excess radiation intensity to have a sample arm filter transmission of 10% or less. For example, in the current assignee's commercial nanoIR™ AFM-based IR spectroscopy instrument, users often use filter transmission coefficients of 10% or even 1% and still achieve sufficient sensitivity. In fact, at higher intensities, it is possible to melt or burn samples at wavelengths with high absorption and/or high source intensity.

One of the key benefits of the current invention is elimination of the need for an in situ reference in order to obtain wavelength dependent spectra. The challenge has been that as wavelength dependent measurements have been performed, there has been an arbitrary an unknown phase offset at each measurement wavelength. As mentioned previously, this has been addressed by creating a phase reference measurement on an in situ reference sample with either flat or known phase behavior. The current invention provides two alternatives to overcome the need for an in situ reference sample. Returning to FIG. 2, we point out some additional features. Repositionable mirror 222 can direct the incident beam in the sample arm 207 such that it is redirected to a sample arm reference mirror 224. Mirror 224 can optionally be positioned by actuator or translation stage 226. Mirror 224 is preferably placed at a distance along the optical path from beam splitter 204 that is the same as the optical path distance from the beam splitter 204 to the probe tip 208. Actuator/translator 226 can be used to adjust and optimize to match these distances. The distances should be equal to within the coherence length of the radiation source and better performance can be achieved with even better matching.

With mirror 222 positioned to direct the sample beam to mirror 224, it is possible to perform a reference measurement of the phase of the light in the sample arm relative to the reference arm. These measurements can be used to create a phase reference table that can be used to correct measurements when mirror 222 is removed, allowing light to be directed towards the sample 209 and probe tip 208. The correction process is shown in FIGS. 8-9 and described shortly. As an alternate to an additional reference mirror, it is possible and in some cases preferable to use an ex situ reference sample. The ex situ reference sample is a sample that has flat and/or known phase behavior and can be occasionally placed in the measurement system in place of a sample of interest. The ex situ sample is measured as one would measure a sample of interest. Analysis of the resulting phase measurements on the ex situ sample results in a phase correction table that can be applied to samples of interest.

Figure 8:
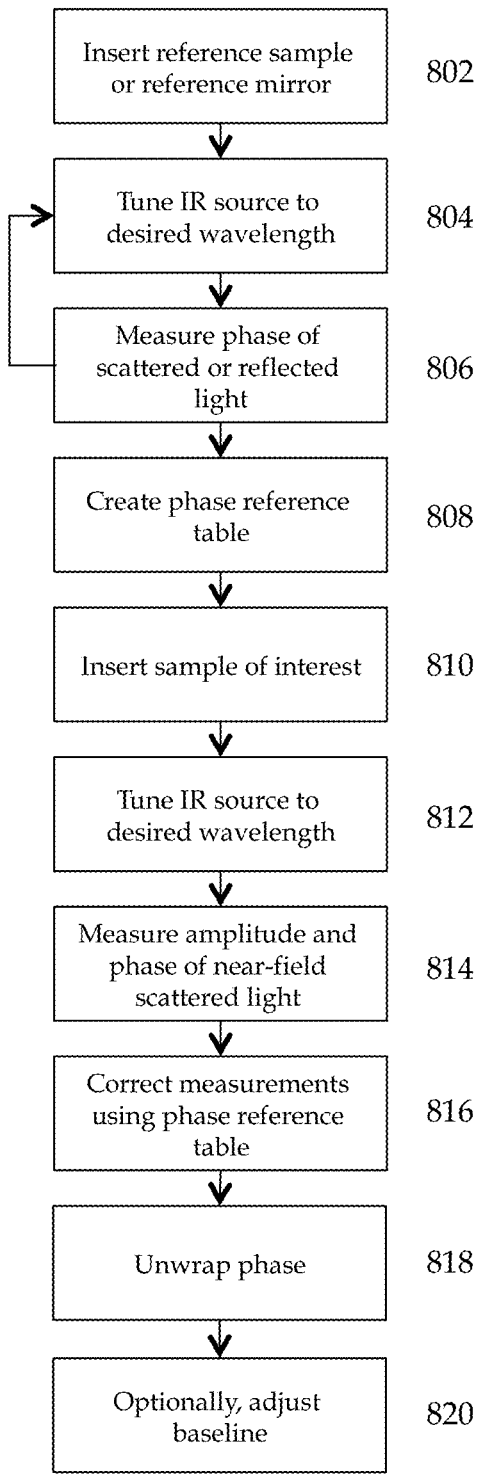
FIG. 8 shows a method under the current invention to obtain a wavelength dependent phase spectrum.

A detailed procedure for eliminating the need for an in situ reference sample is shown in FIGS. 8 and 9. Referring to FIG. 8, the first step 802 involves inserting an ex situ reference sample into the probe microscope or placing an additional reference mirror in the sample arm as described above. Next, step 804, the IR source is tuned to a desired wavelength and optical measurement is performed on light scattered from the ex situ reference sample or light reflected from the sample arm reference mirror. Specifically, a signal indicative of optical phase is measured (step 806). Tuning (804) and measuring optical phase (806) is repeated at all desired wavelengths, typically covering the tuning range of the IR source and with a spectral resolution corresponding to match that used for samples of interest. From the measurements of scattered/reflected radiation, the optical phase is extracted at each desired wavelength and a phase reference table is created (step 808). Next a sample of interest is inserted into the probe microscope (step 810) and the IR light is directed towards the sample of interest (away from the sample arm reference mirror, if used). The IR source is again tuned to a desired wavelength (step 812) and the amplitude and phase of the light scattered from the tip-sample area of the sample of interest is measured (step 814). An illustration of a raw phase spectrum obtained at this point is shown in FIG. 9A. Next the near field optical phase measurement is corrected, by subtracting off the correction values from the phase reference table (step 816), and as illustrated in FIG. 9B. The phase spectrum, even after correction by the phase table has a large number of discontinuities. This is due to the limited output range of inverse tangent functions that are used to calculate phase. These functions have a limited range, for example $\pm\pi/2$ for a tan or $\pm\pi$ for a tan 2. When the measured phase crosses one of these range limits, a discontinuity is observed in the spectrum. These phase discontinuities can be eliminated, however, using a phase unwrapping process. For example the data can be scanned for discontinuities and an appropriate offset of is added or subtracted to points on one side of the discontinuity to eliminate the discontinuity. One suitable phase unwrapping scheme is described by National Instruments, describing their "Unwrap Phase VI," for example at http://zone.ni.com/reference/en-XX/help/371361J-01/lvanls/unwrap_phase/.

Once the phase is unwrapped, a signal resembling a traditional absorption spectrum may be visible at this point, for example in FIG. 9C. The unwrapped spectrum may still have benefit from further processing. In step 820 in FIG. 8, and FIG. 9D, the unwrapped phase can have baseline offset and baseline slope removed. A linear baseline slope can result from a slight optical path difference between the phase reference measurement and a measurement on a sample of interest. In the case of using a sample arm reference mirror (224 in FIG. 2), this optical path difference can result from a difference in the distance between the beam splitter (204 in FIG. 2) and the sample (209) versus the distance between the beam splitter and the sample arm reference mirror. In the case of an ex situ reference sample, the optical path difference can result from the thickness difference between the reference sample and a sample of interest. These optical path differences, however, create a constant propagation time error, resulting in a phase error that is linear with the optical frequency. Thus if the phase is plotted as a function of wavenumber, the phase error will result in a linear slope in the baseline. Thus it is possible to perform a linear fit to the baseline and subtract off this slope. An illustration of the baseline slope adjusted spectrum is shown in FIG. 9D.

An additional embodiment of the current invention includes the use of amplitude modulation. By modulating the amplitude of the reference arm it is possible to create a time/frequency dependence in the ErefEnf term. If the probe is being modulated at a frequency of $\omega 0$ and the reference arm is modulated at $\omega ref$, the ErefEnf will have components at $n\omega 0\pm\omega ref$. Any demodulation technique that extracts one or more components at these frequencies can be used to create a measurement of optical properties of the sample. Amplitude modulation can have several advantages over phase modulation techniques of the prior art. First, phase modulation requires moving a large aperture mirror a reasonable fraction of a wavelength. In practice this requires large piezo actuators with significant current and bandwidth requirements. In practice the maximum oscillation frequency is generally in the range of a few hundred Hz to perhaps low kHz regime for large aperture, high performance mirrors. The limit on modulation frequency puts strict requirements on the bandwidth of any demodulation device. For example, if the reference mirror is modulated at 200 Hz, this modulation will create small sidebands ±200 Hz from the cantilever oscillation frequency and its harmonics. To avoid contamination from the central band, it is necessary to use a narrow band filter and/or a narrow bandwidth demodulation system to isolate the sidebands. Such narrow band demodulation techniques take longer integration times to achieve such filtering. As a result, the measurement time performance of pseudoheterodyne mode (or any mode producing sidebands) depends inversely with demodulation bandwidth. A sideband 200 Hz from a central Fourier peak might require a bandwidth of 50 Hz to achieve good isolation from the central peak, resulting in a measurement time of at least 20 msec per measurement point. For this reason it is highly desirable to employ modulation technique that can be performed at high frequency, thus creating sidebands at much more widely spaced frequencies. Widely spaced sidebands allow high speed demodulation with short integration/filtering times. Under the current invention, amplitude modulation can create sidebands at 10-100× wider frequency separation. Amplitude modulation can be achieved using a variety of techniques. For example, traditional optical choppers can achieve amplitude modulation over 100 kHz. Scitek makes multi-slot choppers that can operate at rates up to at rates up to 120 kHz. Other devices such as photoelastic modulators, deformable micromirrors can also operate up to similar frequencies. Additionally devices such as voice coil fast steering mirrors, galvo mirrors and MEMS micromirrors can steer optical beams at rates from 500 Hz to 10s of kHz. Such steering mirrors can achieve amplitude modulation by periodically steering the reference beam on and off the detector. Any of these amplitude modulation techniques can be employed to achieve sideband separation larger than conventional pseudoheterodyne techniques and thus achieve shorter spectral measurement times and image times.

S-SNOM interference measurements depend critically on the optical phase between the tip scattered light and that of the reference beam. It would be beneficial to obtain measurements of the optical phase variation across a sample or as a function of wavelength. Unfortunately, these measurements are easily compromised by slight path length shifts between the reference arm and the sample arm. These path lengths are sensitive to path temperature and atmospheric variation between the reference arm and the sample arm of the interferometer. For example consider a sample or reference arm with a length of ~100 cm. (This refers to the distance from the diagonal beamsplitter to the tip or reference mirror and back.) A 1 K difference in path temperature for a 100 cm reference arm length and a thermal expansion coefficient around 10-5/K would give a path difference of 10 µm. At a 6 µm wavelength, this path length error would represent an optical phase shift of 600°. This phase error is orders of magnitude larger than the likely measurement data of near-field phase on most samples. Additional errors can be introduced due to air currents or due to temperature dependent changes in refractive index.

Figure 14A:
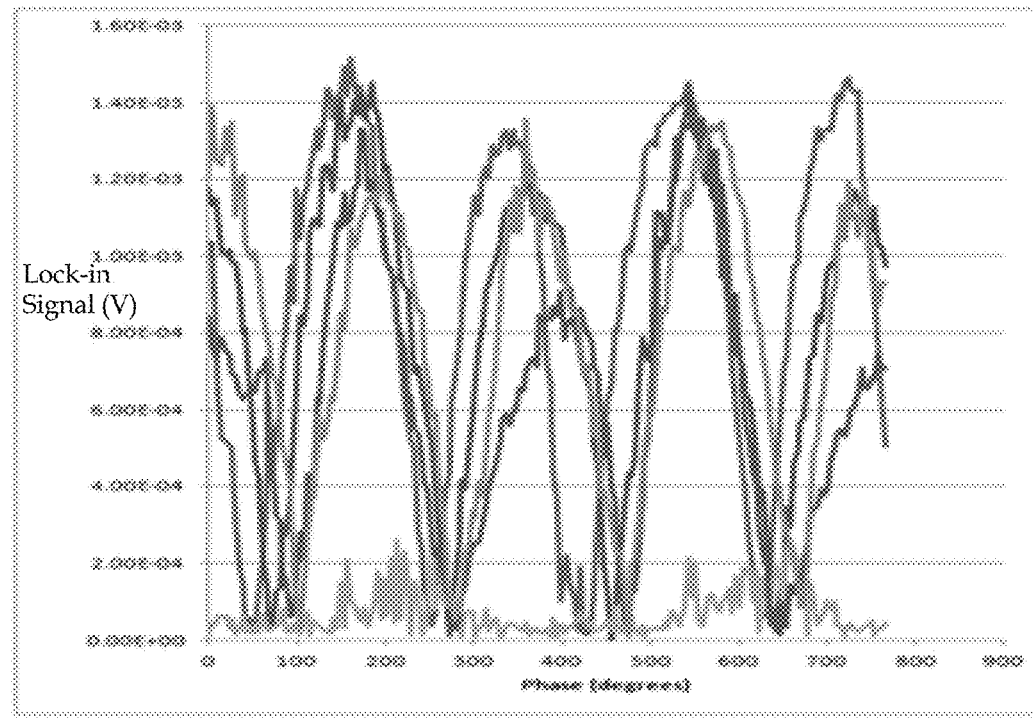
FIGS. 14A and 14B show two examples of data produced by an S-SNOM of the embodiment of FIG. 13.

Example measurements of the phase instability problem of the prior art are shown in FIG. 14A. These interferograms measure the intensity of the light detected at the infrared detector as a function of a reference partial reflector position, effectively moving the reference reflector sequentially through periods of constructive and destructive interference. These measurements were performed using a conventional Michelson interferometer in a typical laboratory environment with the s-SNOM interferometer open to the lab air, i.e. without any enclosure. A series of interferograms were measured over the course of ~5 minutes, resulting in observed phase shifts of almost 90°, e.g. a phase drift rate of ~15-20°/min. The improved results (FIG. 14B), will be discussed below.

Figure 12:
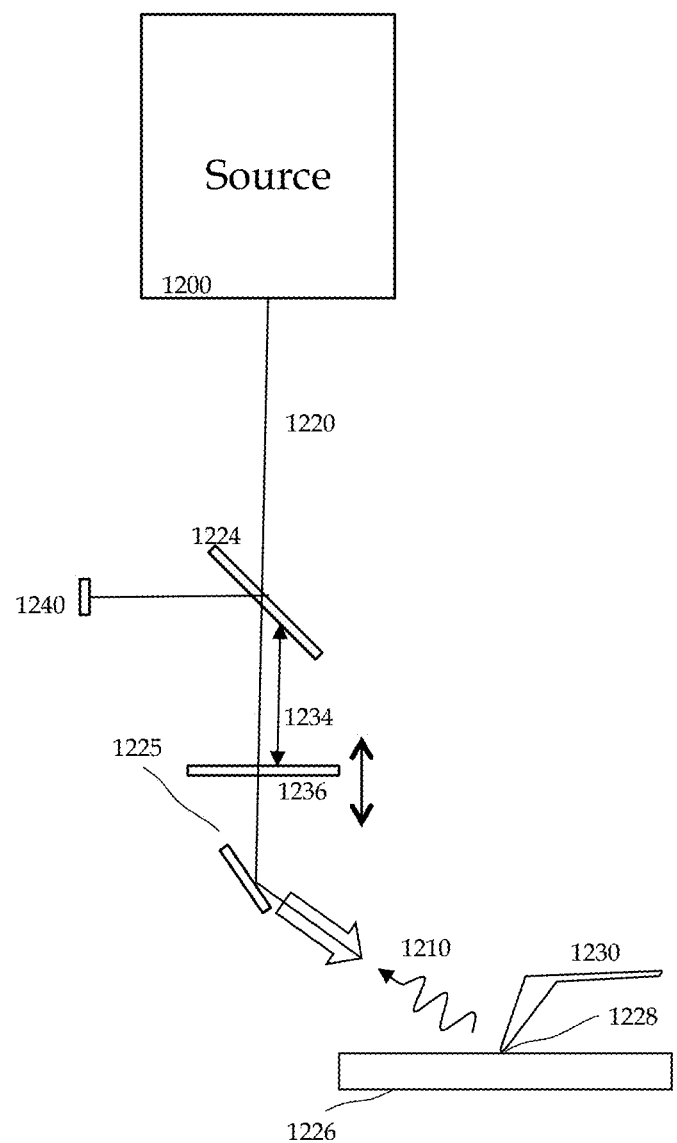
FIG. 12 shows a simplified schematic diagram of an embodiment of an s-SNOM with improved measurement stability.
Figure 13:
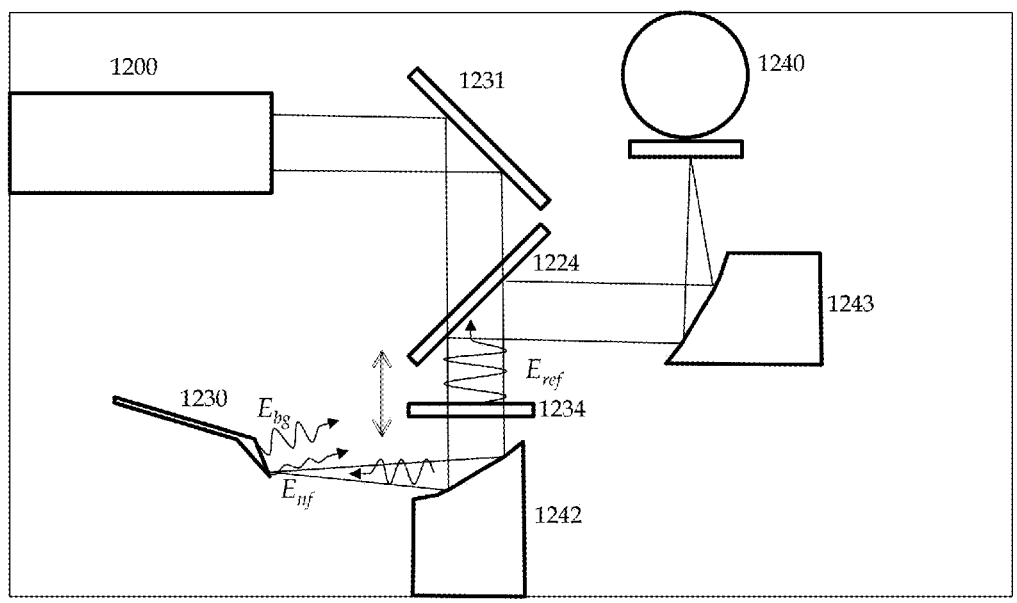
FIG. 13 shows an alternative embodiment to the embodiment of FIG. 12.

An alternative s-SNOM embodiment that may decrease these effects is shown schematically in & FIGS. 12 and 13. In FIG. 12, source 1200, illuminates a probe 1230 sample 1226 interaction region 1228 with radiation 1220 through a beamsplitter 1224, which for illustrative embodiments may be mounted diagonally to the radiation beam. A partial reflector 1236, which may be actuated, is disposed between the beamsplitter 1224 and the tip-sample region 1228, possibly through optional steering optics 1225. Partial reflector 1236 may in some embodiments be disposed substantially normal to the illumination beam 1220 and in some embodiments may be in close proximity to the tip sample region. A portion of the illumination 1210 may be transmitted by partial reflector 1236 to the tip-sample region 1228 forming the sample arm of the interferometer and a portion 1234 may be reflected by the partial reflector 1236 forming the reference arm of the interferometer. The partial reflector may be actuatated to the same degree and by similar mechanisms as described earlier in this application in relation to the reference mirror in the embodiments of FIGS. 1, 2, and 6. The radiation from both the sample and reference arms are directed by beamsplitter 1224 to detector 1240, where the interference product of the light scattered from the tip-sample region and the reference beam are collected and measured.

Unlike the standard s-SNOM interferometer of the prior art, in this embodiment the sample and reference paths of the S-SNOM of FIG. 12 substantially overlap. Because the optical paths are substantially common, any variations in temperature or air currents affect both the sample arm and reference arm almost identically. As a result, unwanted phase shifts from temperature and atmospheric path variations may be greatly reduced. Specifically, the reference and sample paths can be completely overlapped up to the point of the final focusing element.

This embodiment may be particularly advantageous for s-SNOM pseudoheterodyne phase measurements, where phase stability of a few degrees over tens of minutes can be achieved. The S-SNOM embodiment of FIG. 12 may be combined with the other embodiments of this application or may be employed in other s-SNOM systems. Therefore this embodiment also may include the capability of moving the probe to a variety of points on the sample surface to make a map of the collected light. The light source may be a variable wavelength source where the wavelength may be varied over a range of wavelengths during collection to produce a spectrum. The variable wavelength source may vary over a region of the infrared spectrum and the spectrum may be indicative of IR absorption, which in turn is indicative of chemical composition. The mapping and spectral collection may be combined to make a spectral map of the surface, which may be a map of chemical composition.

An alternative and more detailed arrangement of the embodiment of FIG. 12 is shown in FIG. 13. Source 1200 is positioned off-axis and is directed off optional mirror 123 to diagonal beamsplitter 1224 that divides the incident beam into two paths, one reflected and one transmitted. One of these two beams is then sent to partially reflective reference reflector 1234. The partially reflective reference reflector may be arranged substantially perpendicular to the incident beam of radiation in some illustrative embodiments, such that it reflects a portion of the incoming radiation back substantially along the path of incidence. This reflected beam will act as the reference beam that is interfered with tip-sample scattered radiation to allow amplification and/or phase sensitive measurements of the tip scattered radiation. FIG. 13 shows a configuration where the beam transmitted through diagonal beamsplitter is directed to reference reflector 1234. This embodiment can work equivalently with a configuration where the beam reflected by diagonal beamsplitter 1224 is directed to the reference reflector 1234. In any case, the beam transmitted through the reference reflector 1234 is directed to parabolic reflector 1242 to tip 1230, thus allowing tip-sample region to be illuminated by a focused beam of radiation. Light scattered from the tip-sample region is collected by parabolic reflector 1242 and directed back through partial reflector 1234 and back to diagonal beamsplitter 1224. At this point two beams are spatially overlapped: the tip scattered radiation and the reference radiation reflected from the partial reflector 1234. These two beams are then reflected by or transmitted through the diagonal beamsplitter (depending on the configuration) and the light is then directed towards detector 1240. A focusing optic 1243 (for example a parabolic mirror or lens) is optionally used to focus the light onto the surface of detector 1240. The focusing optic 1243 focuses the beams from both the tip-scattered radiation and the reference radiation reflected from the partial reflector 1234 such that the two beams interfere at detector 1240. The reference reflector may be mounted on a translation stage, for example a piezoelectric actuator. The actuator is configured to move the reference reflector substantially in the direction of the incoming beam to adjust the relative phase between the tip scattered light (Enf) and the reference beam reflected from the reference reflector (Eref). By adjusting this phase it is possible to perform interferometric experiments as described previously in this application and other techniques known in the art. For example, it is possible to move the reference reflector between two different phases to obtain two phase homodyne measurements. It is also possible to dither the reference reflector to perform phase modulation/pseudoheterodyne measurements. Further, in one embodiment the reference reflector is mounted on a tip-tilt stage to enable alignment and adjustment of the reference reflector to enable optimal interference at the detector. The tip-tilt stage can be manual or electronically controlled, for example using an actuated mirror assembly, or a fast steering mirror. In one embodiment the reference reflector can be actuated with a voice coil driven fast steering mirror that can provide both alignment and modulation functions. For example the voice coil driven fast steering mirror can be used to modulate the amplitude of the reference beam to perform amplitude modulation experiments.

The embodiments of FIGS. 12-13 arrange the reference arm and the tip-sample arms of the interferometer such that they are substantially spatially overlapped. This is in contrast to the Michelson interferometer traditionally used for s-SNOM experiments where phase modulation is performed in a separate reference arm that does not include the sample arm. The spatially overlapped sample and reference arm ensure that that any temperature or air current disturbances affect these interferometer arms substantially the same, dramatically improving the measurement stability of the system.

Figure 14B:
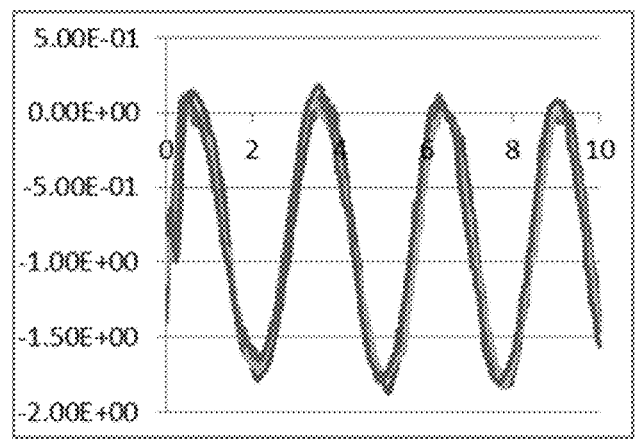

FIG. 14B shows a series of interferograms measured over the course of a few minutes with an s-SNOM if the embodiments of FIGS. 12 and 13. FIG. 14A shows measurements of consecutive interferograms measured with the interferometer similar to FIG. 1A. As mentioned previously, the interferograms of FIG. 14A are not repeatable in an unshielded lab environment due to temperature fluctuations and air currents. FIG. 14B shows improved performance using s-SNOM of FIGS. 12 and 13. In one embodiment the final focus element is an off-axis parabolic mirror with an effective focal length of 2.5 cm. Thus, is possible to reduce the differential path to just over twice this length, for example 6 cm. This arrangement achieves a roughly 17× improvement over the example above. Using the interferometric setup of FIGS. 12-13, interferometric stability of ~1-2°/minute has been achieved in a normal laboratory environment without any temperature stabilizing enclosure.

It is also possible to enclose all or part of the interferometer to protect against air currents. Active temperature control can also be used to achieve very high temperature stability, for example better than 0.1° C. or preferably better than 0.01° C. It is also possible to use low thermal expansion coefficient materials, for example Invar or super-Invar, Zerodur, or other similar materials to construct interferometers that are thermally very stable. Using low thermal expansion materials and a temperature stabilized enclosure is possible to achieve phase stability of better than 0.04°. For example, with a differential path length of 0.06 m and an expansion coefficient of 10-6/K, the differential path would change by 0.06 µm/K. At 6 µm wavelength, this would represent a phase shift of 3.6°/K. Using a temperature stabilized system, and a temperature stability of 0.01 K/min, the differential path change would be 0.6 nm. At 6 µm wavelength, this represents a phase shift of 0.036°/min stable enough to detect even very small optical phase shifts from tip-sample scattered light.

Rapid Point Spectroscopy with a Reference Sample

We now turn to a different embodiment of the current invention. This embodiment is capable of acquiring near field spectra from sub-micron regions of a sample at very high speeds using a tunable narrow band source. This approach overcomes many limitations of prior art s-SNOM, including issues with phase instability, long acquisition times and the need for expensive and complicated laser sources. The approach of this embodiment may be applied to a variety of SNOM arrangements, including those shown in FIGS. 1A and 1B, 2, 12, and 13.

For the novel spectral analysis method, the source for the SNOM is a tunable source, capable of producing radiation over a range of selectable center wavelengths. One such source is a Quantum Cascade Laser (QCL) as described above. Quantum Cascade Lasers are available that are both narrowband yet broadly tunable. For example, QCLs are available from Daylight Solutions that have a linewidth of less than 100 MHz full width half maximum, corresponding to a linewidth of ~0.003 cm$^{-1}$ linewidth when measured in wavenumbers. This is in contrast to broadband sources like picosecond and femtosecond sources have intentionally wide linewidths to cover multiple spectroscopic wavelengths at a time. QCLs in comparison have linewidths that are generally much narrower than a single absorption peak in the mid-infrared for solid materials. Currently available QCL chips also have a tuning range of up to 120 cm$^{-1}$ per QCL chip and this tuning range is growing as the technology matures. Multiple QCL chips can be combined to have tuning ranges cover most of the mid-IR wavelength range. QCLs are also being extended to the THz regime as well.

Using a tunable narrowband light source such as described above, an illumination center wavelength is selected and the probe is placed on a "reference region" on the sample. A reference region should ideally have flat or at least known optical properties over the wavelength range of interest. For example in the case of a constant absorption coefficient over a wavelength range of interest the light scattered from this reference region will have a constant optical phase. Thus the phase measurement on the reference region can act as a constant baseline to act as a reference for measurements on regions of interest on the sample. (Note that unfortunately the word "reference" is used in the s-SNOM literature for two unrelated purposes. In one case it is used to describe the light from the moving mirror arm of the interferometer. So "reference phase" refers to the optical phase of light in this arm. The word reference is also used to describe a sample or a region of a sample that has flat or otherwise known optical properties as described above. To attempt to avoid confusion, we will explicitly specify whether we are referring to the reference arm of the interferometer or a reference region of the sample.)

Figures 15A, 15B:
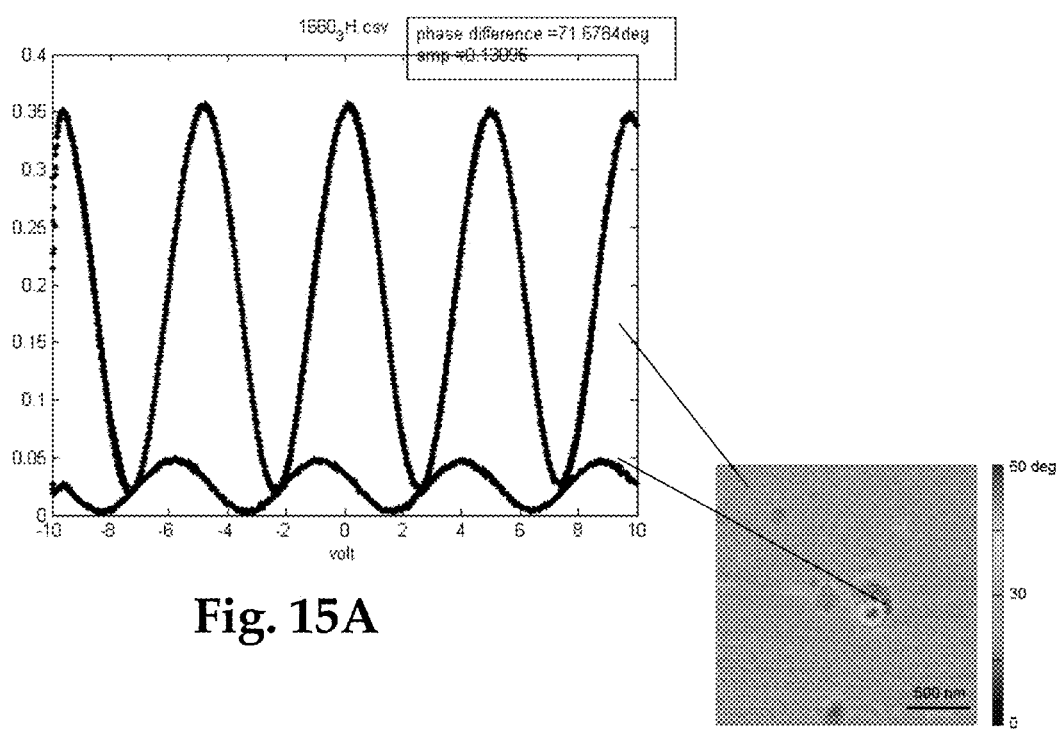
FIGS. 15A and 15B illustrate two interferograms, one acquired from a reference region of a sample of known properties and one acquired from a region to be analyzed.

The relative phase of the reference arm is swept while measuring a signal indicative of the light collected by the detector. The phase sweep may be linear, sinusoidal, or performed at a series of discrete phase points with arbitrary spacing. At the plurality of relative phase points the detector signal may be analyzed to measure the amplitude at the cantilever oscillation frequency, or at a harmonic of the cantilever oscillation frequency and/or one or more sidebands produced by multiple modulations of the cantilever and the reference amplitude or phase. Measuring any of these signals as a function of the reference arm relative phase produces a so called "interferogram." For example, an interferogram of the interaction between the reference and the third harmonic of the tip-scattered light shown in FIG. 15A. Then the probe is translated to the material of interest region, and the other interferogram of FIG. 15A is produced. Note there is both an amplitude and phase shift between the two interferograms. Both shifts are due to the relative optical properties of the two regions.

The relative phase may be adjusted in a variety of ways. One approach is to simply translate the reference mirror in a linear fashion such as a ramp, triangle or sawtooth drive signal applied to the reference mirror, typically a fraction of the center wavelength to several wavelengths. For IR radiation the distance would be on the order of few micrometers to a few 10's of microns, though shorter or longer sweeps can be used. The interferograms in FIG. 15A were acquired with a ramp signal applied to the reference mirror actuator which resulted in a total mirror translation of ~12.5 microns in a fraction of a second to a few seconds time. (Note that the relative optical path difference is twice the reference mirror motion.) It is only necessary to sweep the reference a distance sufficient to get a good mathematical fit to the interferogram. This can require just a fraction of a wavelength to a few wavelengths so adequate interferograms may be acquired very rapidly. Another way to sweep the phase would be to insert objects into the reference beam that effectively changed the reference path length, such as a wheel with a variety of different length transmissive elements rotated through the reference arm, or an electrically active element whose index of refraction or length can be changed in a controllable manner.

To perform this relative measurement, interferograms are collected alternately between one or more regions of interest on a sample and one or more reference regions. An illustrative sample arrangement is shown in FIG. 15B. For this example a sample region to be analyzed may be a material that has been placed on or adjacent to a reference region of constant or at least known optical characteristics. For example a reference region should ideally have a flat or known absorption coefficient over the wavelength range of interest such that the light scattered from this region will have a constant optical phase. As long as the two regions of the sample can be accessed successively by the probe of the probe microscope, e.g. are within the scan range or probe translation range, a novel approach that produces a spectrum very rapidly may be employed. For the case shown in FIG. 15B, a material is placed on a gold or silicon substrate such that the material and bare portions of the substrate are encompassed within the scan range of the microscope, in this case within a 50 micron distance. Such a substrate has no resonant response in IR wavelengths, it is basically reflective, and therefore provides a suitable reference region for an IR absorption analysis of a sample that does have resonant response to IR radiation. Other suitable reference surfaces could be employed as long as their resonant behavior is known in the wavelength region of interest.

Figure 16:
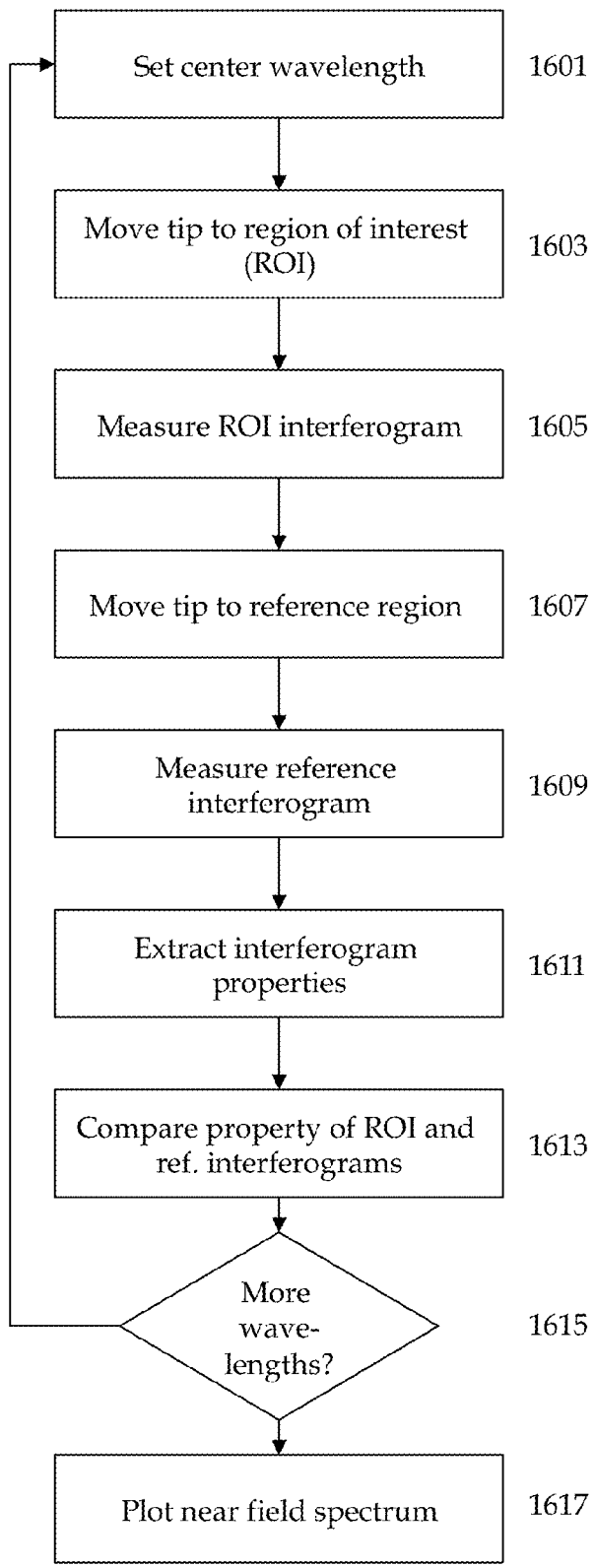
FIG. 16 is a flow chart of an illustrative embodiment
Figure 17A:
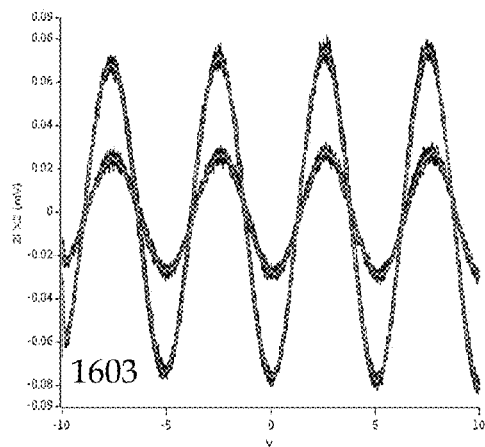
FIGS. 17A, 17B, 17C, 17D, and 17E illustrate a series of inteferograms from a reference region and unknown regions of a sample acquired at different illumination wavelengths.
Figure 17B:
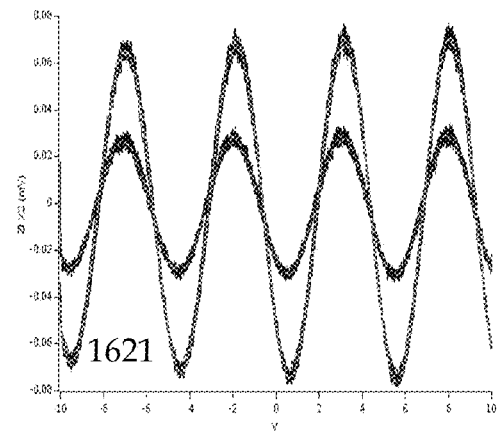
Figure 17C:
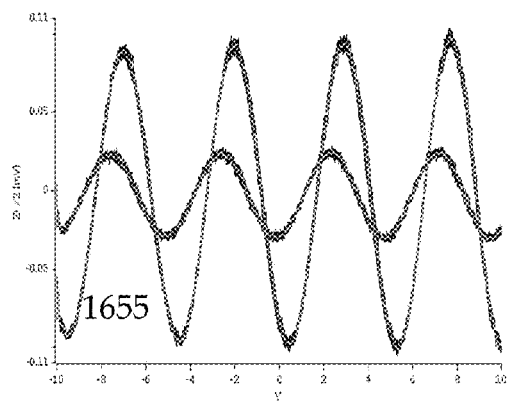
Figure 17D:
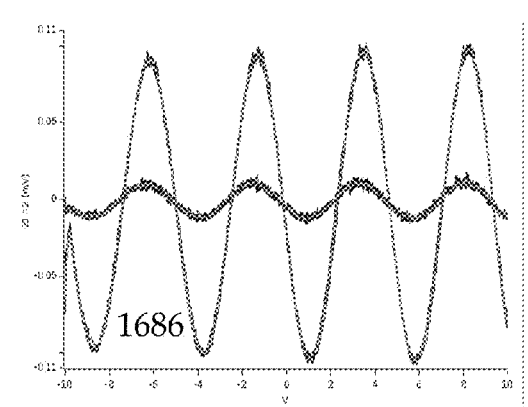
Figure 17E:
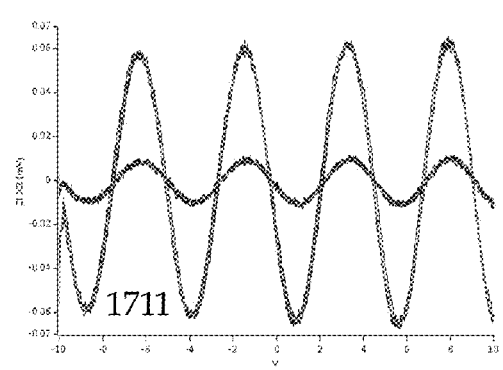

An example measurement flow for one embodiment of the current invention is shown in FIG. 16. First the tunable source is tuned to a desired center wavelength (1601). Next the AFM tip is moved to a region of interest on the sample (step 1603), e.g. a region where a spectroscopic measurement is desired. Next in step 1605 an interferogram is measured on the region of interest by sweeping the relative reference phase. The phase is usually swept at least 180°, e.g. an optical path difference of at least half the wavelength, but shorter and longer phase sweeps can be used, depending on requirements for spectrum signal to noise and instrument sensitivity. After collecting an interferogram on the region of interest, the process is repeated on a reference region of a sample. To repeat the process the AFM tip is moved to a reference region of a sample (step 1607) and the relative reference phase of the interferometer is swept again (step 1609) to create a reference interferogram, i.e. an interferogram on a reference region of the sample. Next the interferograms are analyzed to extract one or more properties of the interferograms (step 1611), such as the amplitude and/or phase of the interferograms. These properties can be obtained by curve fitting techniques, for example, fitting sinusoids to the interferograms. It is also possible to use any number of other techniques, including Fast Fourier Transforms, the Goertzel algorithm, digital lock-in amplifiers or similar techniques that can be used to analyze a sinusoidal signal to extract amplitude and/or phase information. Note that in general the wavelength is well-known for a narrowband light source, so this can be an input to fitting the interferogram to provide faster convergence and/or limit the frequency range that should be analyzed.

Next (step 1613) the properties of the interferograms are compared between the region of interest and the reference region of the sample to create a relative measurement of the light scattered from the region of interest. This comparison/relative measurement can be for example the difference or the ratio between the measurements on the region of interest versus the reference region. In the case where the extracted property is scattered amplitude, the amplitude of light scattered from a region of interest can be divided by the amount of light scattered from a reference region of a sample to get a ratiometric measurement of the relative amount of light scattered by the region of interest. If the scattering properties of the reference region are known, the ratio of scattered amplitude can be used in principal to make absolute measurements of the scattering properties of the unknown region of interest. Additionally it is possible to perform a similar relative measurement of the phase of the scattered light by subtracting the phase of the reference interferogram from the phase of the interferogram on the region of interest. From this comparison it is possible to extract the optical phase shift that resulted from the incident light interacting with the region of interest of the sample under the AFM tip. For certain materials this phase shift may be indicative of absorption coefficient of the region of interest of the sample. More accurate measurements of the absorption coefficient can also be created by using the amplitude and phase of the scattered light and converting these to real and imaginary amplitudes of scattered light. The sample absorption coefficient is more directly related to the imaginary amplitude of the scattered light. More complicated comparison/normalization schemes can also be employed, including those that correct for non-zero or non-flat baselines and algorithms that perform filtering/smoothing, noise suppression on measurements from the region of interest and/or reference regions.

After comparing the properties of the reference and region of interest interferograms at center wavelength steps 1601-1613 are repeated at a plurality of center wavelengths until all desired wavelengths are measured (decision point 1615). By plotting the relative amplitude, phase or other relative property as a function of center wavelength (or equivalently frequency, wavenumber, etc.) a point spectrum of the sub-micron region of the sample is created (step 1617).

Figure 18:
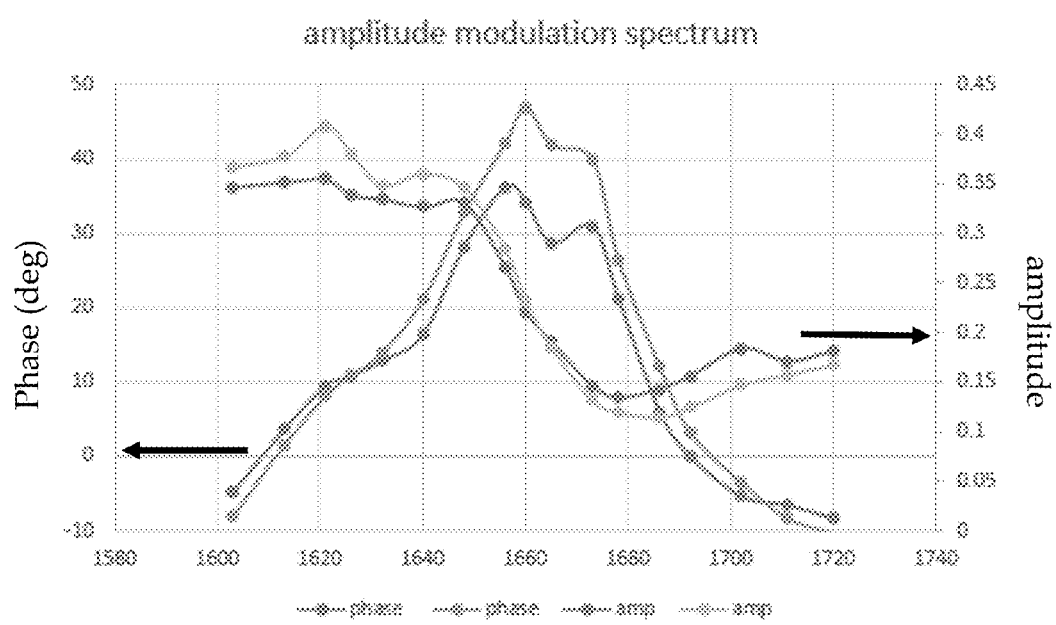
FIG. 18 illustrates deriving an absorption spectrum from the inteferograms of FIGS. 17A-17E by plotting the phase and amplitude differences from the reference region and unknown region interferograms as a function of illumination wavelength.
Figure 19:
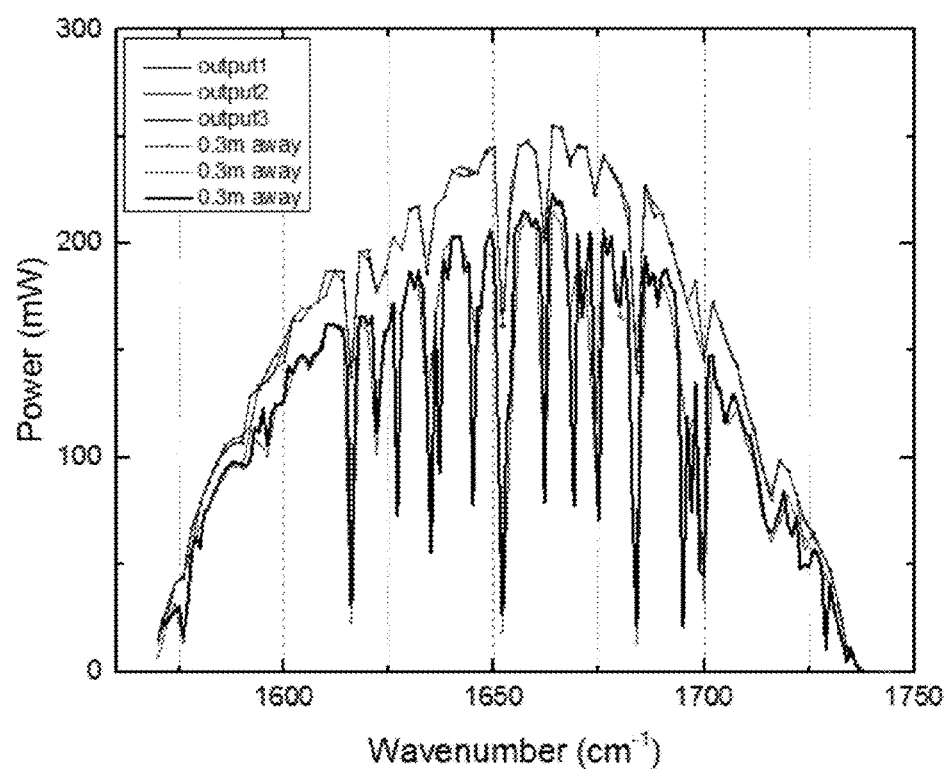
FIG. 19 illustrates power variation of a Quantum Cascade Laser (QCL) illumination source as a function of wavelength.

FIGS. 17A-17E show a series of interferograms on reference regions and regions of interest taken at a plurality of illumination source center wavelengths. (Each interferogram is labeled by the wavenumber ($cm^{-1}$) at which it was measured. "Wavenumber" is a representation of the frequency of the illumination light, inversely related to wavelength, and is commonly used in chemical spectroscopy. The term "plurality of center wavelengths" refers equivalently to a plurality of center wavenumbers.) Note that the interferograms of FIGS. 17A-17E are substantially sinusoidal waveforms. In the case of using a narrowband source per the current embodiment the interferogram is the result of constructive/destructive interference of the scattered light substantially at a single wavelength, thus providing a simple sinusoid. Thus the amplitude and phase shift can be readily seen to vary in each interferogram in FIGS. 17A-17E. The relative phase and amplitude for each wavelength/wavenumber can be analyzed by curve fitting or other techniques described previously. FIG. 18 shows near field spectra from a sub-micron region of interest of a sample, calculated by plotting the relative phase and amplitude calculated from interferograms like those in FIGS. 17A-17E, using measurement and analysis steps of FIG. 16. These plots show relative amplitude and relative phase vs illumination center wavelength for two experiments (two successive sweeps over a range of center wavelengths). The s-SNOM literature has shown that in some cases the relative signal is representative of an absorption spectrum while the amplitude signal shows dispersive behavior. The maximum in the phase spectra correspond at least approximately to the absorption peaks measured by conventional IR spectroscopy, so the positions of phase maxima can be used to identify the material being analyzed.

These point spectra can be created extremely quickly compared to the prior art. The reference mirror can be swept within a fraction of a second to obtain an interferogram. Consider a scenario for example where it takes 1 second each for the following steps (1) Adjust center wavelength; (2) Move tip to region of interest, (3) Capture interferogram on region of interest; (4) Move tip to reference region; (5) capture reference interferogram. In this case the relative optical amplitude or phase for each center wavelength can be acquired in 5 seconds. To create a spectrum with 101 points (say over 400 cm−1 with 4 cm−1 spectral resolution) would take as little as 505 seconds, around 8.4 minutes, still tremendously faster than the prior art spatio-spectral imaging. In practice, however, it is possible to substantially increase the speed of many of these steps. For example it is possible to step and settle between regions of interest and reference regions of the sample within a few milliseconds with a well-designed scanner, especially using fast scan AFM technologies. The same is true for adjusting the center wavelengths on tunable lasers, especially for closely spaced wavelengths as is the case for adjacent wavelengths in an optical spectrum. The most time consuming step can be the time required to acquire the interferogram since the signal levels can be small and slower sweep times can help provide longer signal integration. In the event that the one second is still allocated for each interferograms but the moving and tune times are negligible, the time for each spectrum point is 2 seconds and the total time for a spectrum of 101 points is 202 seconds, or 3.4 minutes. It is also possible to perform continuous scanning of the tunable source such that there is no step and settle time. (In this case the sweep rate of the tunable source is set to a speed such that the wavenumber changes less than the desired spectral resolution during the time required for the interferogram. It is also highly desired in this case that the interferometer arms have very carefully matched optical path lengths so that the small wavelength shifts do not induce phase shifts.) In the case of high signal to noise, for example on materials that are strong light scatterers, it can be possible to measure an interferogram of sufficient quality in as little as a few milliseconds. For example on a sample that is a strong scatterer and using a tunable laser and SPM scanner that are both optimized for rapid sweep and/or rapid step and settle, it is possible to achieve each of these steps in <10 msec: (1) tune wavelength; (2) move tip to region of interest; (3) collect interferogram on region of interest; (4) move to reference region; (5) collect reference interferogram. In this case, a measurement at each center wavelength can be acquired in 50 msec. So a spectrum over 400 cm−1 with 101 points can be obtained in as little as 5050 msec or ~5 sec. These 10 msec/step times can be achieved with careful design of sub-components. Piezoelectric scanning elements are available for example from Piezomechanik that offer ranges in the 10-30 micrometer range with resonance frequencies of a few 10s of kHz. These actuators can be sufficiently damped to achieve settling times in the <10 msec range or even <1 msec. A carefully desired tunable IR sources can also be swept and/or settled in <10 msec/center wavelength. Tuning in such source is usually performed by translating or rotating a nonlinear optical crystal or diffraction grating. These items can be very low mass such that high speed translation/rotation stages may be used for tuning. For example the inventors have built a tunable IR laser using a Dover MMG-50 linear motor stage that could sweep the entire tuning range of 2.5 to 4.5 μm in 80 msec. For angle tuning Newport for example makes rotary stages with accelerations up to 60,000°/sec$^2$ and max velocities of 1000°/sec. Such a stage can rotate 1° (accelerating and decelerating) in ~8 msec. And as mentioned earlier, it is possible to demodulate the third harmonic of the s-SNOM scattered light with a bandwidth of 100 kHz, thus allowing one measurement point every 10 μsec or 200 point interferogram can be obtained in as little time as 2000 μsec. But even with a narrower bandwidth to provide more noise rejection, for example 2 kHz bandwidth can still achieve a 200 point interferogram in as little as 0.1 sec. Thus using the techniques described in this paragraph and earlier related discussion, it is easily possible with the approach of the current invention to achieve acquisition times for point spectra of less than 10 minutes, less than 5 minutes per spectrum, and even less than 1 minute per spectrum. These times are in dramatic contrast this to 8-33 hours required by the prior art to obtain spectra via the prior art technique of s-SNOM spatio-spectral imaging.

This approach benefits from the illumination having narrow bandwidth about each center frequency, less than 8 cm−1 or preferably less than 1 cm−1 because it does not require a long-travel interferometer to achieve high spectral resolution. With a broadband source, e.g. a femtosecond laser it is necessary to use a long travel interferometer to deconvolve broadband response.

The approach of the current invention can also support rapid arrays of point spectra with any arbitrary set of locations. For example it is possible to take an AFM image and then program a set of locations to be measured for point spectra. These locations may be selected arbitrary locations of interest, in a rectangular grid or in a linear array, for example across an interface between two materials. Independent of the array of points, each measurement can be referenced against a measurement automatically performed at a reference location or locations. The reference location is typically programmed into the system by a user, for example using an AFM image to determine a location of a material with substantially constant or otherwise known optical properties over the center wavelength range of interest. The reference interferogram can be measured if desired before and/or after each measurement on a sample region of interest. It is also possible to measure the reference interferograms with less frequency, say every 2nd, 5th or 10th measurement point. The frequency of reference measurement is determined by the thermal stability of the interferometric measurement system. It is desirable to collect a reference interferogram sufficiently frequently such that the phase drift between reference measurements is smaller than the desired noise level. Note that in the flow chart in FIG. 16 the steps are specified for convenience in a specific order. This order, however, does not need to be preserved. For example it is possible to move the tip to a desired location and then tune the center wavelength or the reverse of this. Some of the steps, for example tuning the center wavelength and moving to a new location can be performed in parallel. The interferograms can be performed first on the region or interest or on the reference region. A key element, however, in this embodiment is that one or more regions of interest are identified by a user, point spectra from those regions can be collected automatically from these regions without further user intervention. That is the software automatically moves through a pattern of pattern of collecting interferograms on regions of interest and a reference region over a plurality of center wavelengths. It is not necessary for the user to manually change the wavelength or manually capture the interferograms.

From FIGS. 17A-17E, it can be observed that the reference interferogram varies in amplitude with center wavelength. For a purely reflective surface such a gold, this should not be the case. The reason is that, as shown in FIG. 18, the power output of a QCL varies with center wavelength. Accordingly, it is desirable that the reference interferograms are acquired at each center wavelength. Alternately, it is possible to simply measure the power spectrum from the tunable light source and use that to normalize the amplitude response. In that case it is only necessary to measure the reference interferogram frequently enough to compensate for drifts in the phase, i.e. the relative path difference between the sample arm and reference arm. If the instrument is designed to be extremely thermally stable, i.e. with materials with low thermal expansion coefficients and/ or in a temperature controlled enclosure, it may be necessary to measure the reference interferogram less frequently, e.g once every 10 center wavelengths or once per spectrum. Note that one way to minimize the frequency at which the reference interferograms must be measured is to match the path length extremely accurately for both the sample arm and the reference arm of the interferometer. This is normally not required for narrowband tunable sources, for example QCL sources. A QCL laser with a linewidth of <1 cm$^{-1}$ can have a coherence length of longer than 1 m. So it is possible to collect interferograms with sample and reference arms of significantly different lengths because the beams from the two interferometer arms are still coherent. But even though it is possible to get interferograms, it may not be possible to get good spectra. The reason is that if the sample arm and reference arms have different lengths, the length difference leads to a wavelength dependent phase shift and this phase shift will change as a function of temperature. With a path length mismatch of 5 mm for example and a thermal expansion coefficient of $10^{-5}$/° C. would lead to a path length change of 50 nm/° C., leading to a phase change at 2.5 μm wavelength of $360° \times (50$ nm/2500 nm$)=7.2$°/° C. Since phase spectra on some materials, especially polymeric and biological materials may have small peak amplitudes on the scale of a few degrees it is desirable to perform phase measurements with finer precision. This path length offset, if it were constant over extended times, would just lead to a non-zero phase baseline that could be subtracted out using a static reference phase spectrum acquired on a reference material. But in practice if the interferometer arms experience different temperatures over the course of a measurement, the differential thermal expansion can lead to drifts in relative phase over time that can undermine measurements of phase spectra. That is the phase on the reference material would not be sufficiently stable to act as stable baseline against which to refer the region of interest measurement. As such it is desirable that (1) the reference and sample interferometer arms are as short as possible; (2) the temperature of the two interferometer arms are matched as closely as possible; and (3) the length of the two interferometer arms are matched as closely as possible. Under these conditions (and if the power spectrum of the source is known and stable) it may be possible to measure reference interferograms less frequently. As such the one embodiment of current invention includes an adjustment in the reference arm such that the lengths of the reference and sample arms can be matched very accurately, preferably to less than 1 mm such that temperature variations cause a differential path length change of less than 10 nm/° C. With a path length match of less than 1 mm and a thermal expansion coefficient of $10^{-5}$/° C., this would lead to a path length change of $10^{-5}$ mm=10 nm, leading to a phase change of 1.44°/° C. Low thermal expansion materials $\sim 10^{-6}$/° C. and or active temperature stabilization can reduce this phase change by another order of magnitude. It is also possible through careful adjustment to match the two interferometer arms to better than 0.1 mm or better. This adjustment may be made extremely precisely with a broadband source for example an inexpensive thermal "globar" source. In the case of a broadband source there is a peak in the interferogram around zero optical path difference where all wavelengths are in phase. Adjusting the interferometer to center the reference mirror on the thermal source interferogram peak ensures minimum phase drift for tunable sources. Alternately one can empirically find this point with a tunable narrowband source by observing and minimizing the phase drift via successful measurements of interferograms on the same material. That is the position of the reference mirror is slowly adjusted while measuring the phase drift between successive interferograms. The best adjustment is found at the point where the phase drift is a minimum.

Carefully matching the interferometer arm lengths provides another benefit that is of special significance to tunable light sources. Tunable light sources often use a mechanical element to select the emission wavelength, for example a translation stage or rotary stage to translate or rotate a nonlinear crystal or a diffraction grating. Changing from one center wavelength to another involves a translation/rotation step followed by a period of stabilization during which time the emission wavelength may be changing slightly. The wavelength changes are generally small and may not be significant relative to the desired spectral resolution. But even small wavelength changes can lead to big phase changes if the interferometer path lengths are not accurately matched. For example imagine that a QCL source is being tuned from 1500 cm$^{-1}$ and that during stabilization the output drift by 1 cm$^{-1}$, i.e. from a wavelength of 6667 nm to 6671 nm. This is smaller than most absorption linewidths for solid materials, so by itself this wavelength instability may not be overly detrimental by itself. But with a interferometer path mismatch of even 1 mm, this wavelength stabilization period would result in a phase error of 36° (the difference in the phase for the two wavelengths over 1 mm). This phase error is unacceptably large. With interferometers with even slightly mismatched path lengths it would be necessary to wait for complete stabilization of the wavelength, impacting the measurement time for acquisition of near field point spectra. But if the interferometer arms are matched in path length to 0.1 mm or better the phase drift from this wavelength stabilization issue can be minimized. Of course the required accuracy of the path matching depends on the wavelength drift of the source and larger path length errors can be accommodated with sources with smaller wavelength drifts.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of measuring an optical property of a sub micrometer region of a sample comprising the steps of:
    a. Interacting a probe tip of a probe microscope with a region of interest of the sample;
    b. Illuminating the sample with a beam of light from at least one tunable light source with a center wavelength $\lambda$ such that light is scattered from the probe-sample interaction region,
    c. Interfering a reference beam with the scattered light, wherein the reference beam has an adjustable relative phase;
    d. Collecting with a detector at least a portion of the light resulting from interference between the scattered light and the reference beam;
    e. Sweeping the relative phase between the reference beam phase and the scattered light to create an inteferogram;
    f. Repeating steps a-e on a reference region of a sample to create a reference interferogram;
    g. Determining the difference between the phase of the interferogram measured on the region of interest with the corresponding phase of the reference interferogram;
    h. Repeating steps a-g at a plurality of center wavelengths;
    i. Using the phase difference at the plurality of wavelengths to create a spectrum for the submicron region of the sample.

2. The method of claim 1 wherein the probe tip is automatically moved between the region of interest and the reference region to collect interferograms at each of the plurality of center wavelengths.

3. The method of claim 1 wherein each interferogram is measured in less than five seconds at each center wavelength.

4. The method of claim 1 wherein the spectrum comprises measurements at at least 10 different center wavelengths.

5. The method of claim 1 wherein acquisition of the spectrum is completed in less than 10 minutes.

6. The method of claim 1 wherein acquisition of the spectrum is completed in less than 5 minutes.

7. The method of claim 1 wherein the spectrum has a spectral resolution of 4 $cm^{-1}$ or better.

8. The method of claim 1 wherein the tunable light source is a quantum cascade laser.

9. The method of claim 1 wherein the reference region of the sample comprises a region of the sample within a scan range of the probe microscope that has a substantially flat optical response over the plurality of center wavelengths.

10. The method of claim 1 wherein the tunable source has a full width half maximum bandwidth around the center wavelength of less than 1 $cm^{-1}$.

11. The method of claim 1 wherein the spectrum is measured over a center wavenumber range covering at least 100 $cm^{-1}$.

12. The method of claim 1 wherein the reference beam, the illumination, and the collection are arms of an interferometer.

13. The method of claim 1 wherein one of the probe tip or sample is translated relatively and the steps repeated at a plurality of sample regions to create a spectrum map of the sample.

14. A system for measuring an optical property of a sub micrometer region of a sample comprising a probe microscope with a probe tip, at least one tunable light source, a reference beam source, a detector, a reference beam phase shifter, and a computing control and analysis device, configured to:
    a. Interact the probe tip of the probe microscope with a region of interest of the sample;
    b. Illuminate the sample with a beam of light from the least one tunable source with a center wavelength $\lambda$ wherein light is scattered from the probe-sample interaction region,
    c. Interfere a reference beam with the scattered light;
    d. Collect with the detector at least a portion of the light resulting from interference between the scattered light and the reference beam;
    e. Sweep the relative phase between the reference beam phase and the scattered light to create an inteferogram;
    f. Repeat a-e on a reference region of a sample to create a reference interferogram;
    g. Determine the difference between the phase of the interferogram measured on the region of interest with the corresponding phase of the reference interferogram;
    h. Repeat a-g at a plurality of center wavelengths;
    i. Use the phase difference at the plurality of center wavelengths to create a spectrum for the submicron region of the sample.

15. The system of claim 14 further comprising a scanner configured to automatically move the probe tip between the region of interest and the reference region to collect interferograms at each of the plurality of center wavelengths.

16. The system of claim 15 wherein one of the probe tip or sample is moved relatively and the spectrum is created at a plurality of sample regions to create a spectrum map of the sample.

17. The system of claim 14 wherein each interferogram is measured in less than five seconds at each center wavelength.

18. The system of claim 14 wherein the spectrum comprises measurements at at least 10 different center wavelengths.

19. The system of claim 14 wherein acquisition of the spectrum is completed in less than 10 minutes.

20. The system of claim 14 wherein acquisition of the spectrum is completed in less than 5 minutes.

21. The system of claim 14 wherein the spectrum has a spectral resolution of 4 $cm^{-1}$ or better.

22. The system of claim 14 wherein the tunable light source is a quantum cascade laser.

23. The system of claim 14 wherein the reference region of the sample comprises a region of the sample within a scan range of the probe microscope that has a substantially flat optical response over the plurality of center wavelengths.

24. The system of claim 14 wherein the tunable light source has a full width half maximum bandwidth around the center wavelength of less than 1 $cm^{-1}$.

25. The system of claim 14 wherein the spectrum is measured over a center wavenumber range covering at least 100 $cm^{-1}$.

26. The system of claim 14 wherein the reference beam, the illumination, and the collection are arms of an interferometer.

* * * * *